United States Patent
Demopulos et al.

(10) Patent No.: US 9,855,256 B2
(45) Date of Patent: *Jan. 2, 2018

(54) CYCLOOXYGENASE INHIBITOR AND CALCIUM CHANNEL ANTAGONIST COMPOSITIONS AND METHODS FOR USE IN UROLOGICAL PROCEDURES

(71) Applicant: Omeros Corporation, Seattle, WA (US)

(72) Inventors: Gregory A. Demopulos, Mercer Island, WA (US); Jeffrey M. Herz, Mill Creek, WA (US); Wayne R. Gombotz, Kenmore, WA (US); Hui-rong Shen, Bothell, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/145,453

(22) Filed: May 3, 2016

(65) Prior Publication Data

US 2016/0317515 A1 Nov. 3, 2016

Related U.S. Application Data

(63) Continuation of application No. 14/316,008, filed on Jun. 26, 2014, now abandoned, which is a (Continued)

(51) Int. Cl.
*A61K 31/4422* (2006.01)
*A61K 9/00* (2006.01)
(Continued)

(52) U.S. Cl.
CPC ........ *A61K 31/4422* (2013.01); *A61K 9/0034* (2013.01); *A61K 9/08* (2013.01);
(Continued)

(58) Field of Classification Search
None
See application file for complete search history.

(56) References Cited

U.S. PATENT DOCUMENTS

| | | |
|---|---|---|
| 4,593,044 A | 6/1986 | Metz |
| 4,724,266 A | 2/1988 | Satzinger et al. |

(Continued)

FOREIGN PATENT DOCUMENTS

| | | |
|---|---|---|
| CA | 2206119 | 5/2008 |
| WO | WO 96/19233 | 6/1996 |
| WO | WO 03/086370 | 10/2003 |
| WO | WO 2006/127096 | 11/2006 |

OTHER PUBLICATIONS

Nema et al. "Excipients and Their Use in Injectable Products", PDA J. Pharm. Sci. & Tech., Jul.-Aug. 1997, 51(4), pp. 166-171.*

(Continued)

*Primary Examiner* — Carlos Azpuru
*Assistant Examiner* — Casey Hagopian
(74) *Attorney, Agent, or Firm* — Marcia S. Kelbon

(57) ABSTRACT

Compositions of a cyclooxygenase inhibitor and a calcium channel antagonist in a liquid carrier. The composition may be administered the urinary tract during urological diagnostic, interventional, surgical and other medical procedures. One disclosed composition comprises ketoprofen and nifedipine in a liquid irrigation carrier, and includes a solubilizing agent, stabilizing agents and a buffering agent.

4 Claims, 12 Drawing Sheets

Related U.S. Application Data continuation of application No. 11/384,235, filed on Mar. 17, 2006, now Pat. No. 8,790,696.

(60) Provisional application No. 60/683,488, filed on May 20, 2005.

(51) Int. Cl.

| | |
|---|---|
| *A61K 9/08* | (2006.01) |
| *A61K 31/00* | (2006.01) |
| *A61K 31/192* | (2006.01) |
| *A61K 31/40* | (2006.01) |
| *A61K 31/44* | (2006.01) |
| *A61K 31/455* | (2006.01) |
| *A61L 31/16* | (2006.01) |
| *A61K 31/21* | (2006.01) |

(52) U.S. Cl.
CPC .......... *A61K 31/00* (2013.01); *A61K 31/192* (2013.01); *A61K 31/21* (2013.01); *A61K 31/40* (2013.01); *A61K 31/44* (2013.01); *A61K 31/455* (2013.01); *A61L 31/16* (2013.01); *A61L 2300/402* (2013.01); *A61L 2300/41* (2013.01); *A61L 2300/432* (2013.01)

(56) References Cited

U.S. PATENT DOCUMENTS

| | | | |
|---|---|---|---|
| 4,867,985 | A | 9/1989 | Heafield et al. |
| 4,932,936 | A | 6/1990 | Dykstra et al. |
| 4,966,890 | A | 10/1990 | Gillespie |
| 5,019,601 | A | 5/1991 | Allen et al. |
| 5,409,955 | A | 4/1995 | Bockow et al. |
| 5,512,055 | A | 4/1996 | Domb et al. |
| 5,536,241 | A | 7/1996 | Zapol |
| 5,610,184 | A | 3/1997 | Shahinian, Jr. |
| 5,698,549 | A | 12/1997 | Steers et al. |
| 5,779,661 | A | 7/1998 | Stephen et al. |
| 5,800,385 | A | 9/1998 | Demopulos et al. |
| 5,843,016 | A | 12/1998 | Lugnani et al. |
| 5,858,017 | A * | 1/1999 | Demopulos .......... A61K 9/0019 604/890.1 |
| 5,860,950 | A | 1/1999 | Demopulos et al. |
| 5,912,006 | A | 6/1999 | Bockow et al. |
| 5,962,522 | A | 10/1999 | Wacher et al. |
| 6,242,447 | B1 | 6/2001 | Demopulos et al. |
| 6,261,279 | B1 | 7/2001 | Demopulos et al. |
| 6,420,432 | B2 | 7/2002 | Demopulos et al. |
| 6,645,168 | B2 | 11/2003 | Demopulos et al. |
| 8,790,696 | B2 | 7/2014 | Demopulos et al. |
| 2002/0077328 | A1 | 6/2002 | Hassan et al. |
| 2002/0114838 | A1* | 8/2002 | Ayer .................... A61K 9/0004 424/486 |
| 2002/0198136 | A1 | 12/2002 | Mak et al. |
| 2003/0096801 | A1 | 5/2003 | Demopulos et al. |
| 2003/0096807 | A1* | 5/2003 | Demopulos .............. A61K 9/08 514/215 |
| 2003/0144639 | A1 | 7/2003 | Gehling |
| 2003/0181426 | A1 | 9/2003 | Eisenbach |
| 2004/0142034 | A1 | 7/2004 | Thor et al. |
| 2004/0198775 | A1 | 10/2004 | Fraser et al. |
| 2005/0159403 | A1 | 7/2005 | Stephenson et al. |
| 2006/0263393 | A1 | 11/2006 | Demopulos et al. |
| 2007/0248639 | A1 | 10/2007 | Demopulos et al. |
| 2012/0238940 | A1 | 9/2012 | Demopulos et al. |
| 2014/0212460 | A1 | 7/2014 | Demopulos et al. |

OTHER PUBLICATIONS

Handbook of Pharmaceutical Excipients, 1986, American Pharmaceutical Association, pp. 78-80 and 273-274.*

Rovner, e., et al., "Treatments Used in Women with Interisitial Cystitis: The Interstitial Cystitis Data Base (ICDB) Study Experience," *Urology* 56:940-945 (2000).

Matthiasson, A., et al., "Effects of Intravesical Instillation of Verapamil in Patients with Detrusor Hyperactivity," *Neurourology and Urodynainics: Proceedings of the International Continence Society* 6(3):253-254 (1987) (Abstract only).

Sprem, M., et al., "Intravesically Administered Ketoprofen in Treatment of Detrusor Instability: Cross-over Study," *Croation Medical Journal* 41(4):423-427 (2000).

Ghoniem, G.M., et al., "Clinical Experience with Multiagent Intravesical Therapy in Interstitial Cystitis Patients Unresponsive to Single-agent Therapy," *World J Urol* 11:178-182 (1993).

Jack, D., et al. "Four-drug Regimen Improves IC Pain and QoL Scores," *Urology Times* 29(10):29-30 (2001).

Levin, R.M., et al., "Experimental Hypeneflexia: Effect of Intravesical Administration of Various Agents," *Pharmacology* 42:54-60 (1991).

Levin, R.M., et al., "Intravesical Ketoprofen Inhibits Acetylcholine-Evoked Urinary Bladder Contractility and Hyperreflexia in the Anesthetized Rabbit Model," *Abstract presented at the 2006 Annual Urological Association meeting.*

Soons, P.a., et al., "Analysis of Nifedipine and its Pyridine Metabolite Dehydronifedipine in Blood and Plasma: Review and Improved High-Performance Liquid Chromatographic Methodology," *Journal of Pharmaceutical & Biomedical Analysis* 9(6):475-484 (1991).

Sadana, G.S., et al., "Mechanistic Studies on Photolytic Degradation of Nifedipine by Use of $^1$H-NMR and $^{13}$C-NMR Spectroscopy," *International Journal of Pharmaceutics* 70:195-199 (1991).

Hayase, N., et al., "Newly Discovered Photodegradation Products of Nifedipine in Hospital Prescriptions," *Journal of Pharmaceutical Sciences* 83(4):532-538 (1994).

Bottorff, M.B., et al., "Nifedipine Stability in Cardioplegic Solution," *American Journal of Hospital Pharmacy* 41:2068-2070 (1984).

Leo Pharmaceutical Products, Manufacturer, product *Innohep*, package insert, Jan. 2003.

SICOR Pharmaceuticals, Inc., Manufacturer, product *Dexamethasone*, package insert, Aug. 2003.

Fujisawa Healthcare, Inc., Manufacturer, product *Cyclocort*, package insert, Aug. 2002.

Roerig, a division of Pfizer, Inc, Manufacturer, product *Terramycin*, package insert, Sep. 2003.

Paddock Laboratories, Inc., Manufacturer, product *Norepinephrine Bitartrate Injection, USP*, package insert, May 2004.

Kantor, T.G., et al., "Ketoprofen: A Review of its Pharmacologic and Clinical Properties," *Pharmacotherapy* 6(3):93-103 (1986).

Julou, L., et al., "Ketoprofen (19.583 R.P.) (2-(3-benzoylphenyl)-proprionic acid) Main Pharmacological Properties—Outline of Toxicological and Pharmacokinetic Data," *Scand J Rheumatoloty* 14 Suppl:33-44 (1976).

Forrest, J.B., et al., "Ketorolac, diclofenac, and ketoprofen are equally safe for pain relief after major surgery," *Br J Anaesth* 88(2):227-233 (2002).

Carabaza, A., et al., "Stereoselective inhibition of inducible cyclooxygenase by chiral nonsteroidal antiinflammatory drugs," *J Clin Pharm* 36(6):505-512 (1996).

American Pharmaceutical Association and the Pharmaceutical Society of Great Britain, "Citric Acid and Sodium Metabisulfite," *Handbook of Pharmaceutical Excipients* 78-80, 273-274 (1986).

Nema, S., et al., "Excipients and their use in injectable products," *PDA J Pharm Sci. & Tech* 51(4):166-171 (1997).

Warner, T.D., et al., "Nonsteroid drug selectivities for cyclo-oxygenase-1 rather than cyclo-oxygenase-2 are associated with human gastrointestinal toxicity: A full in vitro analysis," *Proc Natl Acad Sci USA* 96:7563-7568 (1999).

Porpiglia, F., et al., "Effectiveness of Nifedipine and Deflazacort in the Management of Distal Ureter Stones," *Urology* 56:579-583 (2000).

Kostamovaara, P.A., et al., "Ketorolac, diclofenac and ketoprofen are equally efficacious for pain relief after total hip replacement surgery," *British Journal of Anaesthesia* 81:369-372 (1998).

Nankodo, Kabushiki-kaisha. *New Pharmacology* 3:472-480 (1997) (Japanese language).

(56) References Cited

OTHER PUBLICATIONS

Nankodo, Kabushiki-kaisha. *New Pharmacology* 3:472-480 (1997) (Partial English Translation).
Linqing, H. *Chemical Abstracts* 122:642 (1995).
Seitz, C., et al., "Medical therapy to facilitate the passage of stones: What is the eveidence?" *European Urology* 56:455-471 (2009).
Micali, S., et al., "Efficacy of expulsive therapy using nifedipine or tamsulosin, both associated with ketoprofens, after shock wave lithotripsy of ureteral stones," *Urol Res* 35:133-137 (2007).
Staerman, F., at el., "Nifedipine in the medical treatment of symptomatic distal ureteral calculi," *European Urology* 37(Suppl. 2):28 (2000), Meeting abstract.

\* cited by examiner

Rat Bladder Tissue Contractility Agonist Dose-Response

*p<0.05, vs. corresponding pre-treatment values, Dunnett's test.
**p<0.05, vs. vehicle at corresponding time interval, unpaired Student's *t* test

*p<0.05, vs. corresponding pre-treatment values, Dunnett's test.
**p<0.05, vs. vehicle at corresponding time interval, unpaired Student's *t* test Effect of Ketoprofen Pretreatment on Acetic Acid-induced Bladder Hyperactivity

US 9,855,256 B2

CYCLOOXYGENASE INHIBITOR AND CALCIUM CHANNEL ANTAGONIST COMPOSITIONS AND METHODS FOR USE IN UROLOGICAL PROCEDURES

CROSS REFERENCE TO RELATED APPLICATIONS

The present application is a continuation of U.S. patent application Ser. No. 14/316,008, filed Jun. 26, 2014, which is a continuation of U.S. patent application Ser. No. 11/384,235, filed Mar. 17, 2006, now U.S. Pat. No. 8,790,696, which claims the benefit of U.S. Provisional Application No. 60/683,488, filed May 20, 2005.

FIELD OF THE INVENTION

The present invention relates to pharmaceutical compositions for administration to the urinary tract during urological diagnostic, interventional, surgical and other medical procedures and for therapeutic treatment of urologic structures.

BACKGROUND OF THE INVENTION

Many urological procedures are now performed using minimally invasive endoscopic (e.g., cystoscopic or uteroscopic) techniques. These include examination of the urethra, bladder and ureters, therapeutic treatments for benign prostatic hypertrophy, removal or fragmentation of kidney and bladder stones, the placement of urethral or ureteral stents to facilitate the passage of stones, the performance of biopsies and the excision of tumors. While less invasive than open surgery, these techniques involve procedural irritation and trauma to the urinary tract leading to pain, inflammation and smooth muscle spasm. Postoperative lower urinary tract symptoms (LUTS) following urological procedures often include pain, hyperreflexia (unstable bladder contractions), urinary frequency, nocturia and urgency, and in some cases urinary retention requiring prolonged catheterization.

For some surgical procedures, such as transurethral resection of the prostate (TURP), frequent urination and other symptoms resulting from the procedural irritation and inflammation may continue for a prolonged period, gradually resolving during the first six postoperative weeks. For urologic procedures employing a laser, postoperative complications such as inflammation and muscle spasm may continue for several weeks. Patients are frequently prescribed oral anticholinergic medication to inhibit postoperative spasm and reduce the severity of unstable contractions. However, not all patients respond adequately to these drugs, and side effects may lead to discontinuation of these medications.

Urological procedures are often performed with concurrent irrigation of the urinary tract, to remove blood and tissue debris so that a clear endoscopic field of view is maintained. Conventional irrigation solutions include saline, lactated Ringer's, glycine, sorbitol, manitol and sorbitol/manitol. These conventional irrigation solutions do not contain active pharmaceutical agents.

U.S. Pat. No. 5,858,017 to Demopulos, et al., the disclosure of which is hereby incorporated by reference, discloses surgical irrigation solutions and methods for the inhibition of pain, inflammation and/or spasm. The use of irrigation solutions containing pain/inflamation inhibitors and anti-spasm agents during urological procedures in general and during TURP specifically is disclosed, including five-drug and nine-drug combinations. This reference does not teach optimized pairings of a pain/inflammation inhibitory agent with an anti-spasm agent for given urological procedures.

SUMMARY OF THE INVENTION

The present invention provides a locally deliverable composition for inhibiting pain/inflammation and spasm, comprising a combination of ketoprofen and a calcium channel antagonist in a carrier. Ketoprofen and the calcium channel antagonist are each included in a therapeutically effective amount such that the combination inhibits pain/inflammation and spasm at a site of local delivery.

In a further aspect of the present invention, a locally deliverable composition for inhibiting pain/inflammation and spasm comprises a combination of a cyclooxygenase inhibitor and a calcium channel antagonist, propyl gallate as a stabilizing agent and a liquid carrier. Each active agent is included in a therapeutically effective amount such that the combination inhibits pain/inflammation and spasm at a site of local delivery.

In a further aspect of the present invention, a locally deliverable composition for inhibiting pain/inflammation and spasm comprises a combination of a cyclooxygenase inhibitor and a calcium channel antagonist an aqueous liquid carrier, a cosolvent, at least one stabilizing agent and a buffer. Each active agent is included in a therapeutically effective amount such that the combination inhibits pain/inflammation and spasm at a site of local delivery.

A further aspect of the present invention provides a method of inhibiting pain/inflammation and spasm in the urinary tract, comprising delivering to the urinary tract a composition including a combination of ketoprofen and a calcium channel antagonist in a carrier. Ketoprofen and the calcium channel antagonist are each included in a therapeutically effective amount such that the combination inhibits pain/inflammation and spasm in the urinary tract.

A still further aspect of the present invention provides a method of inhibiting pain/inflammation and spasm in the urinary tract during a diagnostic, interventional, surgical or other medical urological procedure, comprising periprocedurally delivering to the urinary tract during a urological procedure a composition including a combination of ketoprofen and nifedipine in a carrier. Ketoprofen and nifedipine are each included in a therapeutically effective amount such that the combination inhibits pain/inflammation and spasm in the urinary tract.

A still further aspect of the present invention provides a method of inhibiting pain/inflammation and spasm in the urinary tract during a urological procedure, comprising periprocedurally delivering to the urinary tract during a ureteroscopic procedure a composition including a combination of a cyclooxygenase inhibitor and a calcium channel antagonist in a carrier. The cyclooxygenase inhibitor and the calcium channel antagonist are each included in a therapeutically effective amount such that the combination inhibits pain/inflammation and spasm in the urinary tract.

A still further aspect of the present invention provides a method of inhibiting pain/inflammation and spasm in the urinary tract during a urological procedure, comprising periprocedurally delivering to the urinary tract during a procedure to remove, fragment or dislodge a kidney or bladder stone a composition including a combination of a cyclooxygenase inhibitor and a calcium channel antagonist in a carrier. The cyclooxygenase inhibitor and the calcium channel antagonist are each included in a therapeutically effective amount such that the combination inhibits pain/inflammation and spasm in the urinary tract.

A still further aspect of the present invention provides a method of inhibiting pain/inflammation and spasm in the urinary tract during a urological procedure, comprising periprocedurally delivering to a urologic structure during a procedure that causes thermal injury to urinary tract tissue a composition including a combination of a cyclooxygenase inhibitor and a calcium channel antagonist in a carrier. The cyclooxygenase inhibitor and the calcium channel antagonist are each included in a therapeutically effective amount such that the combination inhibits pain/inflammation and spasm in the urinary tract.

A still further aspect of the present invention provides a method of inhibiting pain, inflammation and/or spasm in the urinary tract during a urological procedure, comprising periprocedurally delivering to a urologic structure during a ureteroscopic procedure a composition including a combination of a plurality of agents that inhibit pain/inflammation and/or spasm in a carrier. Each agent is included in a therapeutically effective amount such that the combination inhibits pain/inflammation and/or spasm in the urinary tract.

A still further aspect of the present invention provides a method of inhibiting pain, inflammation and/or spasm in the urinary tract during a urological procedure, comprising periprocedurally delivering to a urologic structure during a procedure to remove, fragment or dislodge a kidney or bladder stone a composition including a combination of a plurality of agents that inhibit pain/inflammation and/or spasm in a carrier. Each agent is included in a therapeutically effective amount such that the combination inhibits pain/inflammation and/or spasm in the urinary tract.

A still further aspect of the present invention provides a method of inhibiting pain, inflammation and/or spasm in the urinary tract during a urological procedure, comprising periprocedurally delivering to a urologic structure during a procedure that causes thermal injury to urinary tract tissue a composition including a combination of a plurality of agents that inhibit pain/inflammation and/or spasm in a carrier. Each agent is included in a therapeutically effective amount such that the combination inhibits pain/inflammation and/or spasm in the urinary tract.

BRIEF DESCRIPTION OF THE DRAWINGS

The present invention will now be described in greater detail, by way of example, with reference to the accompanying drawings in which.

DETAILED DESCRIPTION OF THE PREFERRED EMBODIMENTS

Figure 1:
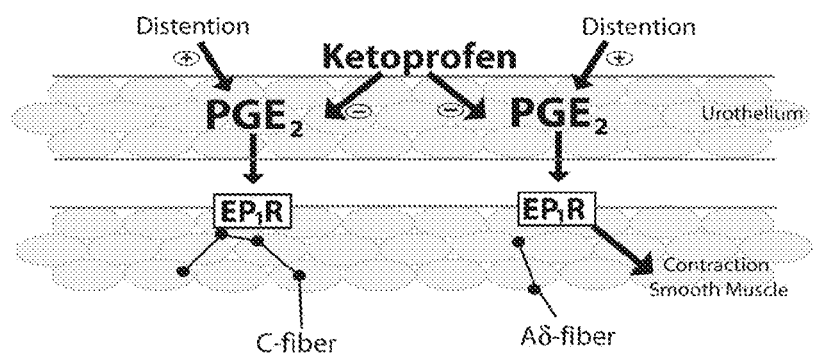
FIG. 1 provides a model for action of prostaglandin activity.

The present invention provides methods and compositions for inhibiting pain, inflammation and/or spasm during urological procedures by locally delivering such compositions to structures of the urological tract during the procedure. The compositions include at least one agent that is a pain/inflammation inhibitory agent or a spasm inhibitory agent, or that acts to inhibit both pain/inflammation and spasm. Preferably, the compositions and methods of the present invention include two or more pain/inflammation inhibitory or spasm inhibitory agents that act on different molecular targets (i.e., enzymes, receptors or ion channels) or that act through different mechanisms of action. More preferably, the compositions of the present invention include at least one pain/inflammation inhibitory agent and at least one spasm inhibitory agent.

As used herein, the term "pain/inflammation inhibitory agent" includes analgesic agents (i.e., antinociceptive agents), non-steroidal agents that inhibit inflammation [including both "non-steroidal anti-inflammatory drugs" (i.e., NSAIDS or cyclooxygenase inhibitors) and other agents that are not steroidal that act to inhibit inflammation], corticosteroids and local anesthetics.

As used herein, the term "spasm inhibitory agent" includes agents that inhibit spasm or contraction of smooth muscle tissue and agents that inhibit spasm or contraction of other muscle tissue associated with the urinary tract (e.g., prostatic muscle tissue).

Another aspect of the present invention is directed to the periprocedural delivery to the urinary tract of a cyclooxygenase (COX) inhibitor, suitably a non-selective COX-1/COX-2 inhibitor, preferably a non-selective COX-1/COX-2 inhibitor that is a propionic acid derivative, more preferably ketoprofen, alone or with at least one additional agent that inhibits pain/inflammation and/or that inhibits spasm, such as a calcium channel antagonist.

Another aspect of the present invention is directed to the periprocedural delivery to the urinary tract of a calcium channel antagonist (i.e., a calcium channel blocker), suitably an L-type calcium antagonist, preferably a dihydropyridine calcium channel antagonist, more preferably nifedipine, alone or with at least one additional agent that inhibits pain/inflammation and/or that inhibits spasm, such as a COX inhibitor.

Another aspect of the present invention is directed to the periprocedural delivery to the urinary tract of a combination of a COX inhibitor and a calcium channel antagonist, preferably a non-selective COX-1/COX-2 inhibitor in combination with an L-type calcium antagonist, more preferably ketoprofen in combination with nifedipine. Ketoprofen and nifedipine have been found by the present inventors to provide greater than additive or synergistic results in the inhibition of bladder spasm, as described in the examples below.

One aspect of the present invention entails the local delivery of the compositions of the present invention to the bladder, ureter, urethra, or other urinary tract structures to inhibit pain, inflammation and/or smooth muscle spasm during urological therapeutic, diagnostic, interventional, surgical and other medical procedures.

As used herein, the terms "urinary tract" and "urinary system" refer to the kidneys, ureters, bladder, urethra and associated nerves, blood vessels and muscles. The term "lower urinary tract" refers to the bladder and urethra and associated nerves, blood vessels and muscles.

A further aspect of the present invention entails the local delivery of the compositions of the present invention to urinary tract structures to reduce postoperative irritative voiding symptoms (e.g., void frequency, nocturia, urgency), pain and/or other lower urinary tract symptoms following such urological procedures.

A further aspect of the present invention entails the local delivery of the compositions of the present invention to urinary tract structures to improve postoperative urinary function (e.g., decrease undesirable urinary retention) following such urological procedures.

The compositions of the present invention are suitably delivered to the urinary tract before, during and/or after urological procedures, i.e., before (pre-) procedurally, during (intra-) procedurally, after (post-) procedurally, pre- and intraprocedurally, pre- and postprocedurally, intra- and postprocedurally or pre-, intra- and postprocedurally.

Preferably, the compositions of the present invention are locally delivered to the urinary tract "periprocedurally", which as used herein means intraprocedurally, pre- and intraprocedurally, intra- and postprocedurally or pre-, intra- and postprocedurally. Periprocedural delivery may be either continuous or intermittent during the procedure. Preferably, the compositions of the present invention are delivered "continuously" during the procedure, which as used herein means delivery so as to maintain an approximately constant concentration of active agent(s) at the local delivery site. When delivered periprocedurally during a surgical procedure, the term "perioperatively" may be used interchangeably with periprocedurally herein. Preferably, the compositions of the present invention are delivered periprocedurely during the period of time when surgical or other procedural trauma and irritation is being incurred by urinary tract tissue.

"Local" delivery of the compositions of the present invention to the urinary tract as used herein refers to delivery of the compositions directly to one or more structures of the urinary tract. The therapeutic agent(s) contained in the locally delivered compositions are not subject to first and/or second pass metabolism before reaching the local site of intended therapeutic (e.g., inhibitory) effect, in contrast to systemically delivered drugs.

Pathophysiologic Effects of Urological Procedures

The trauma of urological procedures results in an acute, localized inflammatory response in the associated urological structures. Inflammation is associated with a complex pattern of biochemical and cellular processes occurring at the local site, involving positive-feedback interactions between the peripheral nervous system, immune cells, the local vasculature and the central nervous system. The inflammatory response to procedural trauma in the urinary tract includes cytokine release, inflammatory cell migration, edema, pain and hyperalgesia.

In response to tissue injury, numerous local mediators are rapidly released, which result in nociceptive stimulation of sensory C-fibers. The inflammatory response triggered by peripheral injury shows that, in addition to cytokines, small G-protein receptor-linked inflammatory mediators also modulate the rapid pathophysiological response of the bladder and urethra. In models of urinary bladder inflammation, bradykinin, histamine, substance P (SP), leukotrienes and prostaglandins have been found to be released from the bladder. Lecci, A., et al., *Pharmacological Analysis of the Local and Reflex Responses to Bradykinin on Rat Urinary Bladder Motility in Vivo*, Br. J. Pharmacol., 114:708-14 (1995); Lecci, A., et al., *Capsaicin Pretreatment Does Not Alter Rat Urinary Bladder Motor Responses Induced by a Kinin B1 Receptor Agonist After Endotoxin Treatment*, Neurosci. Lett. 262:73-76 (1999); Vasko, M., et al., *Prostaglandin E2 Enhances Bradykinin-Stimulated Release of Neuropeptides from Rat Sensory Neurons in Culture*, J Neurosci. 14:4987-97 (1994). Certain inflammatory mediators, such as prostaglandins and kinins, activate and sensitize C-fibers through interaction with specific receptors on nerve terminals. Other inflammatory mediators that have been described in the lower urinary tract include tachykinins and ATP (from C-fibers) (Maggi, C., et al., *Tachykinin Antagonists and Capsaicin-Induced Contraction of the Rat Isolated Urinay Bladder: Evidence for Tachykinin-Mediated Cotransmission*, Br. J. Pharmacol. 103:1535-41 (1991), CGRP (from C-fibers), serotonin (from mast cells and platelets), and endothelin. Maggi, C., et al., *Contractile Responses of the Human Urinary Bladder, Renal Pelvis and Renal Artery to Endothelins and Sarafotoxin S6b*, Gen. Pharmacol. 21:247-49 (1990). These mediators operate together in a synergistic manner to increase postsurgical hyperalgesia, inflammation and muscle spasm. The number of mediators involved in the response underscores the multifactorial origin of the pain and inflammation process.

The immediate activation of the sensory nerves (primary hyperalgesia) triggers a cascade of processes that involves alterations in the local vasculature, and influences muscle contractility. Capsaicin-sensitive afferent fiber stimulation elicits a local efferent response, which is characterized by release of neuropeptides (tachykinins and CGRP) from nerve endings. This release produces a number of local responses, which are part of the pathophysiological effects in the lower urinary tract. These include: (1) direct effects of released neurotransmitters on smooth muscle contraction; (2) changes in microvascular permeability resulting in plasma extravasation and edema of the bladder, urethra and prostate; (3) infiltration of immune cells; and (4) sensitization of nociceptors (secondary hyperalgesia) resulting in increased pain. The consequences of these processes can affect normal bladder capacity and frequency of micturition, and often result in hypersensitivity, pain and smooth muscle spasm.

The pathophysiologic response to procedural trauma of the urinary tract involves a complex cascade of molecular signaling and biochemical changes resulting in inflammation, pain, spasm and lower urinary tract symptoms. These are preferably addressed in accordance with the methods and compositions of the present invention by locally and periprocedurally delivering a combination of pharmacologic agents acting on multiple molecular targets to inhibit pain, inflammation and/or spasm. Preferred agents include cyclooxygenase inhibitors and calcium channel antagonists, more preferably in combination.

Cyclooxygenase Inhibitors

Prostaglandins are produced throughout the lower urinary tract and play a role in neurotransmission, bladder contractility and inflammatory responses. Human bladder mucosa has been found to contain several types of prostaglandins, which have been shown to contract the human detrusor. Prostaglandin $E_2$ ($PGE_2$) is a potent mediator of pain and edema, and the exogenous administration of $PGE_2$ induces contractile responses in inflamed bladders. Intravesical $PGE_2$ produces both urgency and involuntary bladder contractions. Lepor, H., *The Pathophysiology of Lower Urinary Tract Symptoms in the Ageing Male Population*, Br. J Urol., 81 Suppl 1:29-33 (1998); Maggi, C., et al., *Prostanoids Modulate Reflex Micturition by Acting Through Capsaicin-Sensitive Afferents*, Eur. J. Pharmacol. 145: 105-12 (1988). $PGE_2$ given intravesically may stimulate micturition by releasing tachykinins from nerves in and/or immediately below the urothelium. Ishizuka, O., et al., *Prostaglandin E2-Induced Bladder Hyperactivity in Normal, Conscious Rats: Involvement of Tachykinins?*, J Urol. 153:2034-38 (1995). Prostanoids may, via release of tachykinins, contribute to both urge and bladder hyperactivity seen in inflammatory conditions of the lower urinary tract. While not wishing to be limited by theory, these actions are most likely mediated through activation of specific prostanoid receptor subtypes (EP1R) located on C-fibers and on bladder smooth muscle (FIG. 1).

In the inflamed bladder, the basal production of $PGE_2$ is significantly higher than in control conditions. A number of inflammatory mediators acting through GPCR pathways that are linked to the production of arachidonic acid may up-regulate prostaglandin levels in the mucosa and vascular endothelium. Bradykinin is a well-established mediator of inflammation, and bradykinin receptor agonists stimulate greater $PGE_2$ production in inflamed bladders than in control bladders. Topical application of bradykinin activates bladder sensory nerves. Lecci, A., et al., *Kinin B1 Receptor-Mediated Motor Responses in Normal or Inflamed Rat Urinary Bladder in Vivo*, Regul. Pept. 80:41-47 (1999); Maggi, C., et al., *Multiple Mechanisms in the Motor Responses of the Guinea-Pig Isolated Urinary Bladder to Bradykinin*, Br. J. Pharmacol. 98:619-29 (1989). Contractile responses elicited by the selective B1 and B2 receptor agonists tested in isolated rat urinary bladder strips showed that the contractile responses to a selective B1 agonist were also potentiated in inflamed bladders. The role of bradykinin in reflex voiding has also been investigated in normal rats using continuous infusion cystometry. Infusion of bradykinin produced a significant decrease in the intercontraction interval (ICI) between voiding events and an increase in bladder contraction amplitude that is completely blocked by a B2 receptor antagonist.

Microvascular leakage induced by administration of substance P acting through the NK1 receptor also involves the release of cyclooxygenase metabolites of arachidonic acid. Abelli, L., et al., *Microvascular Leakage Induced by Substance P in Rat Urinary Bladder: Involvement of Cyclooxygenase Metabolites of Arachidonic Acid*, J. Auton. Pharmacol. 12:269-76 (1992). These findings demonstrate that distinct inflammatory mediators act through independent receptor mechanisms to trigger the production of prostaglandins. NSAIDs that act at a common target downstream of multiple GPCRs to inhibit COX-1/COX-2 have the capacity to block the formation of prostaglandins derived from multiple proinflammatory mediators.

A number of studies have shown that both COX-1 and COX-2 are involved in the production of $PGE_2$ during tissue trauma and the acute inflammatory response. Martinez, R., et al., *Involvement of Peripheral Cyclooxygenase-1 and Cyclooxygenase-2 in Inflammatory Pain*, J Pharm Pharmacol. 54:405-412 (2002); Mazario, J, et al., *Cyclooxygenase-1 vs. Cyclooxygenase-2 Inhibitors in the Induction of Antinociception in Rodent Withdrawal Reflexes*, Neuropharmacology. 40:937-946 (2001); Torres-Lopez, J., et al., *Comparison of the Antinociceptive Effect of Celecoxib, Diclofenac and Resveratrol in the Formalin Test*, Life Sci. 70:1669-1676 (2002). In normal bladders, activation of B2 receptors evokes bladder contraction mediated by COX-1 activity, whereas COX-2 activity is involved in production of $PGE_2$ driven through stimulation of B1 receptors only. COX-2 is the major isoform that is rapidly expressed and dramatically up-regulated during bladder inflammation. It is believed to be responsible for the high levels of prostanoids released during acute and chronic inflammation of the bladder. COX-2 is up-regulated in response to proinflammatory cytokines and bladder treatment with either endotoxin or cyclophosphamide. Both COX isozymes are therefore suitable molecular targets for the drug compositions of the present invention.

An aspect of the present invention is directed to therapeutic compositions including a cyclooxygenase inhibitor in a carrier suitable for local delivery to urologic structures in the urinary tract. To achieve maximal inhibition of prostaglandin synthesis at sites of acute inflammation, it is believed desirable to inhibit both COX isoenzymes.

The COX inhibitor is therefore preferably non-selective with respect to activity at COX-1 and COX-2, which for purposes of the present invention may be defined as an agent for which the ratio of (a) the concentration of the agent effective for the inhibition of 50% (IC50) of the activity of COX-1 relative to (b) the IC50 for the inhibition of the activity of COX-2 is greater than or equal to 0.1 and less than or equal to 10.0, and more preferably is greater than or equal to 0.1 and less than or equal to 1.0. Suitable assays for determining COX-1 and COX-2 inhibitory effect are disclosed in Riendau, D., et al., *Comparison of the Cyclooxygenase-1 Inhibitory Properties of Nonsteroidal Anti-inflammatory Drugs (NSAIDs) and Selective COX-2 Inhibitors, Using Sensitive Microsomal and Platelet Assays*, Can. J. Physiol. Pharmacol. 75:1088-1095 (1997).

Suitable non-selective COX-1/COX-2 inhibitors include, for purposes of illustration, salicylic acid derivatives including aspirin, sodium salicylate, choline magnesium trisalicylate, salsalate, diflunisal, sulfasalazine and olsalazine, para-aminophenol derivatives such as acetaminophen, indole and indene acetic acids such as indomethacin and sulindac, heteroaryl acetic acids including tolmetin, diclofenac and keterolac, arylpropionic acids including ibuprofen, naproxen, flurbiprofen, ketoprofen, fenoprofen and oxaprozin, anthranilic acids (fenamates) including mefanamic acid and meclofenamic acid, enolic acids including oxicams such as piroxicam and meloxicam and alkanones such as nabumetone, as well as pharmaceutically effective esters, salts, isomers, conjugates and prodrugs thereof.

Still more preferably, the non-selective COX-1/COX-2 inhibitor is an arylpropionic acid, i.e., a propionic acid derivative, such as ketoprofen, dexketoprofen, ibuprofen, naproxen, flurbiprofen, fenoprofen and oxaprozin. Most preferably, the agent is ketoprofen.

In another aspect of the invention, the non-selective COX-1/COX-2 inhibitor used in the compositions and methods of the present invention is selected as having an IC50 for the inhibition of bradykinin-induced bladder smooth-muscle strip contractility (as determined by the bladder contractility model described herein below) of less than or equal to 100 µM, preferably less than or equal to 25 µM, more preferably less than or equal to 5 µM, still more preferably less than 2 µM.

In a further aspect of the invention, the non-selective COX-1/COX-2 inhibitor used in the compositions and methods of the present invention is selected as having an IC50 for the inhibition of bradykinin-induced prostaglandin $E_2$ ($PGE_2$) (as determined by the $PGE_2$ bladder tissue analysis model described herein below) of less than or equal to 100 µM, preferably less than or equal to 25 µM, more preferably less than or equal to 5 µM, still more preferably less than 2 µM.

In a still further aspect of the invention, the non-selective COX-1/COX-2 inhibitor used in the compositions and methods of the present invention is selected as having (a) an IC50 for the inhibition of bradykinin-induced bladder smooth-muscle strip contractility (as determined by the bladder contractility model described herein below) of less than or equal to 100 µM, preferably less than or equal to 25 µM, more preferably less than or equal to 5 µM, still more preferably less than 2 µM, and (b) an IC50 for the inhibition of bradykinin-induced $PGE_2$ (as determined by the $PGE_2$ bladder tissue analysis model described herein below) of less than or equal to 100 µM, preferably less than or equal to 25 µM, more preferably less that or equal to 5 µM, still more preferably less than 2 µM.

The above noted IC50 concentrations are not to be interpreted as limitations on drug concentrations in the compositions of the present invention, which may suitably be determined by the concentrations needed to approach maximal effectiveness and thus may be higher than the IC50 levels.

In a still further aspect of the invention, the non-selective COX-1/COX-2 inhibitor used in the compositions and methods of the present invention is selected as having a $pA_2$ (antagonist potency) of greater than or equal to 7, wherein $pA_2$ is the negative logarithm of the concentration of antagonist that would produce a 2-fold shift in the concentration response curve for an agonist, and is a logarithmic measure of the potency of an antagonist. This potency corresponds to an equilibrium dissociation constant $K_D$ of less than or equal to 100 nM.

In a still further aspect of the invention, the non-selective COX-1/COX-2 inhibitor used in the compositions and methods of the present invention exhibits 50% of maximal inhibitory response in less than or equal to 10 minutes in a kinetic study of bradykinin-stimulated $PGE_2$ response in the $PGE_2$ bladder tissue analysis model described herein below.

Ketoprofen

Unless used in a context also referring to its isomer, references herein to the use of ketoprofen (i.e., m-benzoylhydratropic acid or 3-benzoyl-α-methylbenzeneacetic acid) in the present invention are to be understood to also include pharmaceutically acceptable isomers thereof, including its racemic S-(+)-enantiomer, dexketoprofen, pharmaceutically acceptable salts or esters thereof, and pharmaceutically acceptable prodrugs or conjugates thereof. Ketoprofen is a preferred COX inhibitor for use in the present invention.

Ketoprofen exhibits potent anti-inflammatory, analgesic, and antipyretic actions that are associated with the inhibition of prostaglandin synthesis and antagonism of the effects of bradykinin. Ketoprofen non-selectively inhibits the activity of COX-1 and COX-2, which results in the blockade of prostaglandin production, particularly that of $PGE_2$, preventing the development of hyperalgesia. Ketoprofen has an $IC_{50}$ value of 4-8 nM in a non-selective COX assay, being functionally 6-12 times more potent than other NSAIDs evaluated (e.g., naproxen or indomethacin). Kantor, T., *Ketoprofen: A review of its Pharmacologic and Clinical Properties*, Pharmacotherapy 6:93-103 (1986). Ketoprofen also has functional bradykinin antagonist activity, its effects being eight times greater than those seen with the classical NSAID, indomethacin. Julou, L., et al., *Ketoprofen (19.583 R.P.) (2-(3-Benzoylphenyl)-propionic acid). Main Pharmacological Properties—Outline of Toxicological and Pharmacokinetic Data*, Scand J Rheumatol Suppl. 0:33-44 (1976).

In addition to inhibiting cyclooxygenase, ketoprofen is believed to offer the additional anti-inflammatory benefit of inhibiting lipoxygenase. Ketoprofen has also been found to synergise with nifedipine in the inhibition of bladder spasm, as discussed in greater detail in the examples below.

Calcium Channel Antagonists

Multiple inflammatory mediators, including bradykinin, are released into the bladder in response to tissue injury, which can trigger smooth muscle contraction and spasm. The tone of the urinary bladder smooth muscle is regulated by numerous contraction-promoting receptor systems. They include well established systems such as muscarinic, purinergic and tachykinin receptors [Anderson, K., et al., *Pharmacolgy of the Lower Urinary Tract: Basis for Current and Future Treatments for Urinary Incontenance* Pharmacol Rev. 56:581-631 (2004)], and also include endothelin receptors [Afiatpour, P., et al., *Development Changes in the Functional, Biochemical and Molecular Properties of Rat*

Bladder Endothelin Receptors, Naunyn Schmiedebergs Arch. Pharmacol. 367:462-72 (2003)], protease-activated receptors and bradykinin receptors [Kubota, Y., et al., *Role of Mitochondria in the Generation of Spontaneous Activity in Detrusor Smooth Muscles of the Guinea Pig Bladder*, J. Urol. 170:628-33 (2003); Trevisani, M., et al., *Evidence for In Vitro Expression of B1 Receptor in the Mouse Trachea and Urinary Bladder*, Br. J. Pharmacol. 126:1293-1300 (1999)]. Because many of these receptors are prototypically coupled via $G_q$ proteins to the activation of a phospholipase C (PLC), it is likely that bladder contraction elicited by such receptors is partly mediated by PLC-linked mobilization of $Ca^{2+}$ from intracellular stores [Ouslander, J. G., *Management of Overactive Bladder*, N. Engl. J. Med., 350:786-99 (2004)].

Neurally mediated contractions of the bladder and urethral smooth muscle require mobilization of intracellular $Ca^{2+}$ as well as an influx of extracellular $Ca^{2+}$. $Ca^{2+}$ entry through L-type calcium channels can contribute to muscle contractions by triggering the intracellular release of $Ca^{2+}$, which opens ryanodine-sensitive $Ca^{2+}$ release channels in the sarcoplasmic reticulum. Opening of L-type calcium channels in bladder muscle also serves to replace intracellular $Ca^{2+}$ stores after contraction. Recent studies conclude that muscarinic receptor subtype signaling mediated via carbachol-induced contraction of rat bladders largely depends on $Ca^{2+}$ entry through L-type calcium channels and, perhaps, PLD, $PLA_2$ and store-operated $Ca^{2+}$ channels. Schneider, T., et al., *Signal Transduction Underlying Carbachol-Induced Contraction of Rat Urinary Bladder: I. Phospholipases and Ca2+ sources*, J Pharmacol Exp Ther (2003). Thus, blockade of L-type $Ca^{2+}$ channels has the potential to depress neural, urothelial and smooth muscle evoked contractions of bladder strips mediated by a multiplicity of endogenous GPCR agonists. The L-type calcium channel represents a point of integration for the convergence of multiple inflammatory mediators that can lead to hyperactive smooth muscle contractility.

$Ca^{2+}$ channels located in afferent and efferent nerve terminals in the lower urinary tract are also important for regulation of neurotransmitter release. de Groat, W., et al., *Pharmacology of the Lower Urinary Tract*, Annu. Rev. Pharmacol Toxicol. 41:691-721 (2001). A number of active agents produce $Ca^{2+}$ influx and transmitter release from the peripheral nerve endings of capsaicin-sensitive afferent neurons through voltage-sensitive $Ca^{2+}$ channels. Under certain conditions, L-type $Ca^{2+}$ channels can also contribute to transmitter release.

The significant role of the L-type $Ca^{2+}$ channel in the initiation of smooth muscle contraction makes this channel a potential therapeutic target for the treatment of lower urinary tract problems that involve hyperactivity or spasm of smooth muscle tissues. In the presence of inflammatory mediators, signaling through these same channels may mediate bladder hyperactivity and spasm.

An aspect of the present invention is thus directed to therapeutic compositions including a calcium channel antagonist in a carrier suitable for delivery to urologic structures in the urinary tract. The calcium channel antagonist is preferably an L-type calcium channel antagonist, such as verapamil, diltiazem, bepridil, mibefradil, nifedipine, nicardipine, isradipine, amlodipine, felodipine, nisoldipine and nimodipine, as well as pharmaceutically effective esters, salts, isomers, conjugates and prodrugs thereof. Still more preferably, the calcium channel antagonist is a dihydropyridine, such as nifedipine, nicardipine, isradipine, amlodipine, felodipine, nisoldipine and nimodipine, as well as pharmaceutically effective esters, salts, isomers, conjugates and prodrugs thereof. Most suitably, the agent is nifedipine.

Nifedipine

References herein to nifedipine, 1,4-dihydro-2,6-dimethyl-4-(2-nitrophenyl)-3,5-pyridinedicarboxylic acid dimethyl ester, are to be understood to also include pharmaceutically acceptable isomers thereof, pharmaceutically acceptable salts or esters thereof, and pharmaceutically acceptable prodrugs or conjugates thereof. Nifedipine is a preferred calcium channel antagonist for use in the present invention.

Nifedipine is a member of the dihydropyridine class of calcium channel antagonists with pharmacological specificity for the L-type channel (alternatively termed the Cav1.2 α-subunit). Nifedipine has a rapid onset of action (less than 10 minutes), which is desirable for use in urological procedures, and as such is more preferred than certain closely related dihydropryidine calcium channel antagonists (e.g., amlodipine) that require longer periods for initial action. The time to response for steady-state inhibition of muscle contraction ideally occur within 10-15 minutes of initial local drug delivery, and nifedipine fulfills this criterion.

Carriers

The pain/inflammation and/or spasm agents of the present invention are suitably delivered in solution or in suspension in a liquid carrier, which as used herein is intended to encompass biocompatible solvents, suspensions, polymerizable and non-polymerizable gels, pastes and salves. Preferably, the carrier is an aqueous irrigation solution that may or may not include physiologic electrolytes, such as saline, distilled water, lactated Ringer's solution, glycine solutions, sorbitol solutions, manitol solutions or sorbital/manitol solutions. The carrier may also include a sustained release delivery vehicle, such as microparticles, microspheres or nanoparticles composed of proteins, liposomes, carbohydrates, synthetic organic compounds, or inorganic compounds.

The compositions of the present invention may also be coated on ureteral and urethral stents, catheters, radioactive seeds, seed spacers and other implantable devices and on surgical instruments, for local delivery from such devices and instruments into the urinary tract as further described below. Polymers that may be suitably employed to form a drug impregnated stent or other implantable device include, by way of non-limiting example, poly(D,L-lactic acid) (PDLLA), poly(lactide-co-glyocide) (PLGA), poly(L-lactic acid) (PLLA), poly(glycolic acid), poly(6-hydroxycaproic acid), poly(5-hydroxyvaleric acid), poly(4-hydroxybutyric acid), poly(ethylene glycol), poly(ethylene oxide)-poly(propylene oxide)-poly(ethylene oxide) (PEO-PPO-PEO, Pluronics™) block copolymers, and copolymers and blends of the above.

Suitable materials for use in producing drug coated stents, catheters, other implantable devices and instruments include biodegradable polymers and polymeric hydrogels, such as by way of nonlimiting example, Pluronics™ triblock copolymers, PLLAs or their copolyesters, poly(glycolic acid) or their copolyesters, poly(ethylene oxide)-cyclodextrin (polyrotaxan) hydrogels, poly[(R)-3-hydroxybutyrate]-poly(ethylene oxide)-cyclodextrin hydrogels, cellulose acetate, cellulose acetate butyrate, cellulose acetate propionate, and cellulose nitrate; polyurethane resins, including the reaction product of 2,4-tolylene diisocyanate, 4,4'-diphenylmethane diisocyanate, polymethylenepolyphenyl isocyanate, or 1,5-napthylene diisocyanate with 1,2-polypropylene glycol, polytetramethylene ether glycol, 1,4-butanediol, 1,4-butylene glycol, 1,3-butylene glycol, poly(1,4-oxybutylene)glycol, caprolactone, adipic acid esters, phthalic anhydride, ethylene glycol, 1,3-butylene glycol, 1,4-butylene glycol or diethylene glycol; acrylic polymers such as ethyl and methyl acrylate and methacrylate; condensation polymers such as those produced by sulfonoamides such as toluenesulfonamide and aldehydes such as formaldehyde; isocyanate compounds; poly(ortho esters); poly(anhydrides); polyamides; polycyanoacrylates, poly(amino acids), polycarbonate), cross-linked poly(vinyl alcohol), polyacetals, polycaprolactone. In addition to these biodegradable polymers, suitable non-biodegradable polymers include polyacrylates, polystyrenes, polyvinyl chloride, ethylene-vinyl acetate copolymers, polyvinyl fluoride, poly(vinyl imidazole) and chlorosulphonated polyolefins.

The pain/inflammation and/or spasm inhibitory compositions of the present invention can also include excipients or adjuvants for enhanced uptake, release, solubility and stability. Aspects of formulating the compositions of the present invention are discussed below.

Additional Agents

The cyclooxygenase inhibitor, calcium channel antagonist or combination cyclooxygenase inhibitor plus calcium channel antagonist compositions of the present invention may include alternate or additional agents that inhibit pain, inflammation and/or spasm. Suitable agents include those disclosed in U.S. Pat. No. 5,858,017 to Demopulos.

In particular, suitable alternate or additional anti-inflammation/anti-pain agents include serotonin receptor antagonists, (e.g., amitriptyline, imipramine, trazodone, desipramine, ketanserin, tropisetron, metoclopramide, cisapride, ondansetron, yohimbine, GR127935, methiothepin), serotonin receptor agonists (e.g., buspirone, sumatriptan, dihydroergotamine, ergonovine), histamine receptor antagonists (e.g., promethazine, diphenhydramine, amitriptyline, terfenadine, mepyramine (pyrilamine), tripolidine), bradykinin receptor antagonists (e.g., [Leu$^8$] des-Arg$^9$-BK, [des-Arg$^{10}$] derivative of HOE 140, [leu$^9$] [des-Arg$^{10}$] kalliden, [D-Phe$^7$]-BK, NPC 349, NPC 567, HOE 140), kallikrien inhibitors (e.g., aprotinin), tachykinin receptor antagonists, including neurokinin$_1$ receptor subtype antagonists (e.g., GR 82334, CP 96.345, RP 67580) and neurokinin$_2$ receptor subtype antagonists (e.g., MEN 10.627, L 659.877, (±)-SR 48968), calcitonin gene-related peptide (CGRP) receptor antagonists [e.g., αCGRP-(8-37)], interleukin receptor antagonists, (e.g., Lys-D-Pro-Thr), phospholipase inhibitors including PLA$_2$ isoform inhibitors (e.g., manoalide) and PLCγ isoform inhibitors (e.g., 1-[6-((17β-3-methoxyestra-1,3,5(10)-trien-17-yl)amino)hexyl]-1H-pyrrole-2,5-dione), lipooxygenase inhibitors, (e.g., AA 861), prostanoid receptor antagonists including eicosanoid EP-1 and EP-4 receptor subtype antagonists and thromboxane receptor subtype antagonists, (e.g., SC 19220), leukotriene receptor antagonists including leukotriene B$_4$ receptor subtype antagonists and leukotriene D$_4$ receptor subtype antagonists, (e.g., SC 53228), opioid receptor agonists, including μ-opioid, δ-opioid and κ-opioid receptor subtype agonists, (e.g., DAMGO, sufentanyl, fentanyl, morphine, PL 017, DPDPE, U50,488), purinoceptor agonists and antagonists including P$_{2X}$ receptor antagonists and P$_{2Y}$ receptor agonists, (e.g., suramin, PPADS), adenosine triphosphate (ATP)-sensitive potassium channel openers, (e.g., cromakalim, nicorandil, minoxidil, P 1075, KRN 2391, (−)pinacidil), neuronal nicotinic agonists (e.g., (R)-5-(2-azetidinyl methoxy)-2-chloropyridine (ABT-594), (S)-5-(2-azetidinyl-methoxy)-2-chloro-pyridine (S-enatiomer of ABT-594), 2-methyl-3-(2-(S)-pyrrolidinyl-methoxy)-pyridine (ABT-089), (R)-5-(2-Azetidinyl methoxy)-2-chloropyridine (ABT-594), (2,4)-Dimethoxybenzylidene anabaseine (GTS-21), SIB-1765F, RJR-2403), 3-((1-methyl-2(S)-pyrrolidinyl)methoxy)pyridine (A-84543), 3-(2(S)-azetidinylmethoxy)pyridine (A-85380), (+)-anatoxin-A and (−)anatoxin-A (1R)-1-(9-Azabicyclo [4.2.2]non-2-en-2-yl)-ethanoate fumarate, (R,S)-3-pyridyl-1-methyl-2-(3-pyridyl)-azetidine (MPA), cystisine, lobeline, RJR-2403, SIB-1765F, GTS-21, ABT-418), α$_2$-adrenergic receptor agonists [e.g., clonidine, dexmedetomidine, oxymetazonline, (R)-(−)-3'-(2-amino-1-hydroxyethyl)-4'-fluoro-methanesulfoanilide (NS-49), 2-[(5-methylbenz-1-ox-4-azin-6-yl)imino]imidazoline (AGN-193080), AGN 191103; AGN 192172, 5-bromo-N-(4,5-dihydro-1H-imidazol-2-yl)-6-quinoxalinamine (UK14304), 5,6,7,8-tetrahydro-6-(2-propenyl)-4H-thiazolo[4,5-d]azepin-2-amine (BHT920), 6-ethyl-5,6,7,8-tetrahydro-4H-oxaazolo[4,5-d]azepin-2-amine (BHT933), 5,6-dihydroxy-1,2,3,4-tetrahydro-1-naphyl-imidazoline (A-54741)], mitogen-activated protein kinase (MAPK) inhibitors (e.g., 4-(4-fluorophenyl)-2-(4-methylsulfinylphenyl)-5-(4-pyridyl)-1H-imidazole, [4-(3-iodo-phenyl)-2-(4-methylsulfinylphenyl)-5-(4-pyridyl)-1H-imidazole], [4-(4-fluorophenyl)-2-(4-hydroxyphenyl)-5-(4-pyridyl)-1H-imidazole], [4-(4-fluoro-phenyl)-2-(4-nitrophenyl)-5-(4-pyridyl)-1H-imidazole], 2'-Amino-3'-methoxy-flavone), soluble receptors (e.g., tumor necrosis factor (TNF) soluble receptors, interleukin-1 (IL-1) cytokine receptors, class I cytokine receptors, and receptor tyrosine kinases), corticosteroids (e.g., cortisol, cortisone, prednisone, prednisolone, flurdrocortisone, 6α-methylprednisolone, tramcinolone, betamethasone, dexamethasone) and local anesthetics (e.g., benzocaine, bupivacaine, chloroprocaine, cocaine, etiodocaine, lidocaine, mepivacaine, pramoxine, prilocaine, procaine, proparacaine, ropivacaine, tetracaine, dibucaine, QX-222, ZX-314, RAC-109, HS-37).

Suitable alternate or additional spasm inhibitory agents include serotonin receptor antagonists (e.g., amitriptyline, imipramine, trazodone, desipramine, ketanserin, tropisetron, metoclopramide, cisapride, ondansetron, yohimbine, GR127935, methiothepin, oxymetazoline), tachykinin receptor antagonists including neurokinin$_1$ receptor subtype antagonists (e.g., GR 82334, CP 96.345, RP 67580) and neurokinin$_2$ receptor subtype antagonists (e.g., MEN 10.627, L 659.877, (±)-SR 48968), adenosine triphosphate (ATP)-sensitive potassium channel openers, (e.g., cromakalim, nicorandil, minoxidil, P 1075, KRN 2391, (−)pinacidil), nitric-oxide donors, (e.g., nitroglycerin, sodium nitroprusside, SIN-1, SNAP, FK 409 (NOR-3), FR 144420 (NOR-4), endothelin receptor antagonists, (e.g., BQ 123, FR 139317, BQ 610) and anticholinergics, including antimuscarinics (e.g., ditropan, tropicamide, cyclopentolate, scopolamine, atropine, homatropine and oxybutynin), antinicotinics (e.g., trimethaphan, macamylamine, pentolinium, pempidine and hexamethomium) and first generation antihistamines (e.g., diphenhydramine).

Methods of Use

Periprocedural Delivery

Local perioperative delivery of the compositions of the present invention are expected to preemptively inhibit pain, inflammation and smooth muscle spasm otherwise associated with urological procedures. The compositions of the present invention act on molecular targets, i.e., receptors, enzymes and ion channels, that initiate pain, inflammation and spasm pathways and mechanisms. The present invention employs local periprocedural delivery to inhibit these pathophysiologic processes at the time they are initiated. For example, multiple proinflammatory peptides stimulate the release of $PGE_2$ from bladder tissue within the first five minutes of exposure, as shown in the examples below. Solely postprocedurally administered therapeutic agents can only take effect after these processes have commenced.

Local Delivery

Local delivery of drugs in accordance with the present invention permits the utilization of a much lower dosage than would be needed if the same drugs were administered systemically (e.g., orally, intravenously, intramuscularly, subcutaneously) to achieve the same predetermined local level of inhibitory effect in the urinary tract. The focused, local delivery of the present invention results in a significantly lower plasma level of the drug than would result from systemic delivery of the drug to achieve the same predetermined local level of inhibitory effect in the urinary tract, thereby reducing the potential for undesirable systemic side effects. Local delivery permits the inclusion in the compositions of the present invention of drugs such as peptides that are not susceptible to systemic delivery due to degradation during first- and second-pass metabolism.

Local delivery of drug compositions in accordance with the present invention provides for an immediate and certain therapeutic concentration at the local urinary tract site, which is not dependent on variations in metabolism or organ function. A constant concentration of the drugs can be maintained during the period of delivery of the composition during the procedure.

Urological Procedures

The compositions of the present invention can be locally delivered before, during and/or after cystoscopy, i.e., the endoscopic examination of the urethra and bladder through a cystoscope inserted into the lower urinary tract for purposes of examining the urinary tract structures, preferably periprocedurally during such procedures. The compositions of the present invention may also be used before, during and/or after (preferably periprocedurally during) other diagnostic, interventional, medical and surgical procedures performed in conjunction with cystoscopy, by insertion of surgical instruments through the cystoscope, such as for the removal of tissue for biopsy, removal of growths, removal of foreign bodies, bladder or kidney stone removal, placement, removal and manipulation of urethral stents, transurethral resection of bladder tumors (TURBT), treatment of tumors with electrocautery or laser or local chemotherapeutics, treatment of bleeding in the bladder or to relieve obstructions in the urethra.

The compositions of the present invention can be locally delivered to the urinary tract before, during and/or after ureteroscopy, i.e., the endoscopic examination of the ureters and renal tissues through an ureteroscope inserted through the urethra and bladder and into a ureter for purposes of examining the urinary tract structures, preferably periperatively during such procedures. Ureteroscopy is often performed for the drawing of urine samples from each kidney, the placement, removal and manipulation of ureteral stents, as part of the treatment for kidney stones, or to place a catheter in the ureter for a retrograde pyelography, and the compositions of the present invention can be delivered before, during and/or after such procedures, preferable periprocedurally during such procedures. A basket or other instrument employed via the ureteroscope can be used to capture the stone, the stone may be broken up by laser or shock wave lithotripsy through the ureteroscope, or the ureteroscope may be employed to displace a lodged stone back into the kidney for subsequent breaking up and passage, such as by using a laser or extracorporeal shock wave lithotripsy (ESWL).

The compositions of the present invention are suitably locally delivered to the urinary tract before, during and/or after procedures that typically result in ureteral spasm, such as kidney stone removal using laser treatment, cystoscopy, ureteroscopy or lithotripsy, and preferably periprocedurally during such stone removal procedures.

The compositions of the present invention may also be locally delivered to the urinary tract before, during and/or after (preferably periprocedurally) urological procedures that cause thermal trauma to tissue in and/or associated with the urinary tract. These include laser treatment to fragment stones or ablate tissue, microwave ablation of tissue (e.g., transurethral microwave thermotherapy (TUMT) to remove prostatic tissue), radiofrequency ablation of tissue (e.g., transurethral needle ablation (TUNA) to remove prostatic tissue), electrocauterization or vaporization of tissue or cryoblation of tissue.

The compositions of the present invention may also be locally delivered to the urinary tract before, during and/or after (preferably periprocedurally) urological procedures employing a laser for tissue resection, including Holmium: yttrium-aluminum-garnet (Ho:YAG), neodymium:yttrium-aluminum-garnet (Nd:YAG) and potassium-titanyl-phosphate (KTP) "green light" laser therapies. Such laser procedures may include the treatment of benign prostatic hyperplasia (BPH) and bladder tumors, by way of non-limiting example.

The ketoprofen composition, calcium channel antagonist and ketoprofen combination composition and the preferred ketoprofen and nifedipine combination composition of the present invention may also be locally delivered to the urinary tract before, during and/or after (preferably periprocedurally) transurethral resection of the prostate (TURP).

In addition to transurethral procedures such as those discussed above, the compositions of the present invention may also be suitably employed for local delivery during other minimally invasive urological procedures. These include, by way of example, the transrectal or transperitoneal delivery of the compositions of the present invention to the prostate and surrounding anatomic structures during implantation of radioactive seeds and seed spacers to treat prostate cancer or prostatitis, and the transrectal or transperitoneal delivery of the compositions of the present invention to the prostate to treat prostatitis.

The compositions of the present invention are suitably locally delivered to the urinary tract before, during and/or after (preferably periprocedurally) procedures that standardly include irrigation, such as TURP, transurethral incision of the prostate (TUIP), laser prostatectomy, cystoscopy, ureteroscopy and other procedures in which irrigation is used to aid visualization by removing blood and tissue debris from the operative field. The compositions of the present invention can be added to the irrigation solution standardly used in such procedures, e.g., saline, distilled water, lactated Ringer's solution, glycine, sorbitol, manitol, sorbital/manitol, at dilute levels, with no change to the urologist's standard procedure being required.

The compositions of the present invention can also be locally delivered by coating ureteral stents, urethral stents, catheters, radioactive seeds, seed spacers or other implantable devices or surgical instruments, or impregnating or otherwise incorporating the therapeutic agents into the body of stents, catheters, radioactive seeds, seed spacers or other implantable devices or surgical instruments constructed from a polymeric material or mesh. Techniques for coating devices with drugs and impregnating devices with drugs are well known to those of ordinary skill in the art, and coatings or polymeric materials may be designed to permit the drugs (e.g., a COX inhibitor and a calcium channel antagonist) to begin releasing into the urinary tract upon implantation and continuing for a period of time following implantation.

Formulation

One aspect of the invention is directed to a composition including a cyclooxygenase inhibitor and a calcium channel antagonist, preferably ketoprofen and nifedipine, which are dissolved in an aqueous solution for parenteral delivery, preferably for intravesicular delivery. Alternately such compositions can be manufactured in a lyophilized form and then reconstituted with an aqueous solvent prior to administration.

The cyclooxygenase inhibitor and calcium channel antagonist are suitably included in a molar ratio (cyclooxygenase inhibitor:calcium channel antagonist) of from 10:1 to 1:10, preferably from 5:1 to 1:5, more preferably from 4:1 to 1:1, and most preferably 3:1. Similarly, in a preferred composition ketoprofen and nifedipine are suitably included in a molar ratio (ketoprofen:nifedipine) of from 10:1 to 1:10, preferably from 5:1 to 1:5, more preferably from 4:1 to 1:1, and most preferably approximately (i.e., +/−20%) 3:1.

For compositions formulated to be delivered locally in a liquid carrier, the cyclooxygenase inhibitor such as ketoprofen is suitably included at a concentration (as diluted for local delivery) of no more than 500,000 nanomolar, preferably no more than 300,000 nanomolar, more preferably no more than 100,000 nanomolar and most preferably less than 50,000 nanomolar. The calcium channel antagonist such as nifedipine is suitably included at a concentration (as diluted for local delivery) of no more than 200,000 nanomolar, preferably no more than 100,000 nanomolar, more preferably no more than 50,000 nanomolar and most preferably less than 25,000 nanomolar.

The compositions of the present invention may be formulated in an aqueous or organic solvent, but preferably are formulated in an aqueous solvent. When using aqueous solutions, an additional solvent or solvents (i.e., cosolvents or solubilizing agents) may suitably be included to aid in dissolution of the drugs. Examples of suitable solvents include polyethylene glycol (PEG) of various molecular weights (e.g., PEG 200, 300, 400, 540, 600, 900, 1000, 1450, 1540, 2000, 3000, 3350, 4000, 4600, 6000, 8000, 20,000, 35,000), propylene glycol, glycerin, ethyl alcohol, oils, ethyl oleate, benzyl benzoate, and dimethyl sulfoxide (DMSO). A preferred cosolvent for the compositions of the present invention is PEG, most preferably PEG 400.

In a further aspect of the present invention, the composition includes ketoprofen and nifedipine in an aqueous solution including at least one stabilizing agent. The term stabilizing agent is used herein to refer to an agent that inhibits degradation of the active pharmaceutical ingredients and/or extends the duration of stability of the solution when stored under either refrigerated (e.g., 2-8° C.) or ambient temperature conditions, and includes both anti-oxidants and chelating agents. The solution may also suitably include one or more cosolvents or buffering agents. Preferably the aqueous ketoprofen and nifedipine solution includes one or more antioxidants as stabilizing agent(s), a cosolvent and a buffering agent. The preferred ketoprofen and nifedipine solution formulation is stable when stored at between 2° C. and 25° C. for a period of at least six months, preferably one year, more preferably two years, most preferably longer than two years, and can be readily diluted with standard urologic irrigation solutions for local intravesicular delivery during urological procedures.

Examples of suitable antioxidants for use as stabilizing agents in the compositions of the present invention include water soluble antioxidants such as sodium bisulfite, sodium sulfite, sodium metabisulfite, sodium thiosulfate, sodium formaldehyde sulphoxylate, □ ascorbic acid, acetylcysteine, cysteine, thioglycerol, thioglycollic acid, thiolactic acid, thiourea, dithithreitol, and glutathione, or oil soluble antioxidants such as propyl gallate, butylated hydroxyanisole, butylated hydroxytoluene, ascorbyl palmitate, nordihydroguaiaretic acid and α-tocopherol. A preferred stabilizing agent for the present invention is propyl gallate. When included in an aqueous composition, a cosolvent is included solubilizing oil soluble antioxidants such as propyl gallate. A preferred aqueous ketoprofen and nifedipine composition of the present invention includes PEG 400 as a cosolvent and propyl gallate as a stabilizing agent, and may more preferably also include a second stabilizing agent such as a water soluble antioxidant, most preferably sodium metabisulfite. A suitable range of concentrations for antioxidant(s) is typically about 0.001% to about 5%, preferably about 0.002% to about 1.0%, and more preferably about 0.01% to about 0.5%, by weight of the composition.

Because of the involvement of divalent cations in catalyzing oxidation reactions, the inclusion of a chelating agent as a stabilizing agent may be useful in the compositions of the present invention. Examples of suitable chelating agents for use in the compositions of the present invention include the various salts of ethylenediamine tetraacetic acid salts (EDTA), β-hydroxyethylenediaminetriacetic acid (HEDTA), diethylenetriamine-pentaacetic acid (DTPA) and nitrilotriacetate (NTA).

The compositions of the present invention suitably include a buffering agent to maintain pH. Examples of suitable buffering agents for inclusion in the compositions of the present invention include acetic acid and its salts, citric acid and its salts, glutamic acid and its salt and phosphoric acid and its salts. Citric acid also has the ability to chelate divalent cations and can thus also prevent oxidation, thereby serving two functions as both a buffering agent and an antioxidant stabilizing agent. A preferred aqueous ketoprofen and nifedipine composition of the present invention includes citric acid (such as in the form of sodium citrate) as a buffering agent and antioxidant, and in a more preferred composition also includes PEG 400 as a cosolvent and propyl gallate and sodium metabisulfite as stabilizing agents.

The compositions of the present invention may also include additional excipients and adjuvants. Excipients may include a preservative to protect against microbial growth, especially for multiple-dose containers. Suitable excipients include antimicrobial agents such as benzyl alcohol, chlorobutanol, thimiserol, methyl paraben and propyl paraben. Excipients may also include a surfactant to reduce surface tension and thereby facilitate wetting for dissolution.

Examples of suitable surfactants include polyoxyethylene sorbitan monooleate and sorbitan monooleate. Excipients may also include tonicity adjustment agents to render the solution iso-osmotic with physiologic fluids. Examples of suitable tonicity agents include sodium chloride, sodium sulfate, mannitol, glucose, sucrose, trehalose, and sorbitol. Additional excipients may include a colorant to impart color, such as FD& C No. 1 blue dye, FD&C No. 4 red dye, red ferric oxide, yellow ferric oxide, titanium dioxide, carbon black, and indigo tar pigments.

TABLE 1

Exemplary Ketoprofen/Nifedipine Composition for Delivery to the Urinary Tract (Stock Solution Concentrations Prior to Dilution)

| Ingredient | Function | Exemplary Concentration/Amount |
| --- | --- | --- |
| Ketoprofen | COX inhibitor | 7.63 mg/ml (30 mM) |
| Nifedipine | CA channel antag. | 3.46 mg/ml (10 mM) |
| Sodium citrate aqueous solution | Buffered solvent | 20 mM solution (pH 6.2 ± 0.5) |
| PEG 400 | Solubilizing agent (cosolvent) | 60% PEG 400: 40% Sodium citrate soln. (v:v) |
| Sodium metabisulfite | Antioxidant (stabilizer) | 0.02% |
| Propyl gallate | Antioxidant (stabilizer) | 0.01% |

The above concentrated solution is diluted, such as at a ratio of 1:1,000 (v:v) with standard irrigation solution such as saline or lactated Ringer's solution. The final dilute solution from the above exemplary formulation thus includes 0.06% PEG40, 0.00005% sodium metabisulfite and 0.00001% propyl gallate (all by volume). The active ingredients are present in the final dilute solution at concentrations of 0.00763 mg/ml (30,000 nM) for ketoprofen and 0.00346 mg/ml (10,000 nM) for nifedipine.

EXAMPLES

The present invention may be illustrated by the following studies demonstrating the effects of ketoprofen and other cyclooxygenase inhibitors, nifedipine and combinations of these agents in urological models, and demonstrating the stability of certain formulations of such compositions.

Example I

The Effect of COX Inhibitors on Bradykinin Induced $PGE_2$ Production in Rat Bladders The following studies evidence that bradykinin induces immediate prostaglandin $E_2$ ($PGE_2$) production in the bladder, and demonstrate the effects of cyclooxygenase inhibitors on this process. Bradykinin was chosen as the activating agonist for testing in this system because its actions on the rat bladder tissue system have been well characterized and because its role as a proinflammatory agent in acute pathophysiology has been studied. Bradykinin is also known to stimulate contraction of smooth muscle of the bladder when delivered intravesically by activation of B1 and B2 receptor subtypes.

1. Introduction

Acute, localized inflammatory responses in the lower urinary tract, including spasm, are triggered by surgical trauma. In response to tissue injury, multiple inflammatory mediators, including bradykinin and Substance P (SP) are released into the bladder. Exogenous application of these pro-inflammatory peptides or activation of bladder nerves can trigger the production of prostaglandins (PGs) in the bladder. The aim of this study was to characterize the time course of production of PGs in response to an inflammatory mediator and evaluate the effects of COX-1/COX-2 inhibitors on bladder tissue contractility in vitro and in vivo. The rat bladder tissue strip system represents a well established system for characterization of the pharmacological actions on numerous agents on smooth muscle bladder contractility [Edwards, G., et al., *Comparison of the Effects of Several Potassium-Channel Openers on Rat Bladder and Rat Portal Vein In Vitro*, Br. J. Pharmacol. 102:679-80 (1991); Birder, L., et al., *β-adrenoceptor Agonists Stimulate Endothelial Nitric Oxide Synthase in Rat Urinary Bladder Urothelial Cells*, J. Neurosci. 22:8063-70 (2002)].

2. Bladder Strip Contractility

Method

Isolated bladder smooth muscle strips of 1×2×15 mm dimension were obtained from Wistar derived male or female rats weighing 275±25 g that were sacrificed by $CO_2$ overexposure. Each strip was placed under 1 g tension in a 10 ml bath containing Krebs solution with 1 µM enalaprilic acid (MK-422), composition (g/l): NaCl 6.9, KCl 0.35, $KH_2PO_4$ 0.16, $NaHCO_3$ 2.1, $CaCl_2$ 0.28, MgSO 4.7, $H_2O$ 0.29, (+)Glucose 1.8, pH 7.4 bubbled with 95% $O_2$/5% $CO_2$ at 32° C. Each strip was connected to an isometric transducer (Harvard, #50-7293) and two-pen recorder and allowed to equilibrate for 60 minutes. Before starting the experiment, mounted tissues were validated for acceptance by challenge with 100 µM of methoxamine to obtain a minimum of 1 g tension, which was considered as 100%. Qualified tissues were washed repeatedly every 15 minutes for 60 minutes. A cumulative contraction-response curve to bradykinin was then generated through application of 3 concentrations of bradykinin (0.01 µM, 0.1 µM and 1 µM) at 1 minute intervals for a total of 3 minutes. The tissue was subsequently washed periodically until tension returned to baseline value. Two hours later, the ability to inhibit the bradykinin cumulative dose response (0.01 µM, 0.1 µM and 1 µM) after a 10 minute pretreatment with ketoprofen was determined. Each concentration of test substance was tested in four separate preparations.

Results

Figure 2:
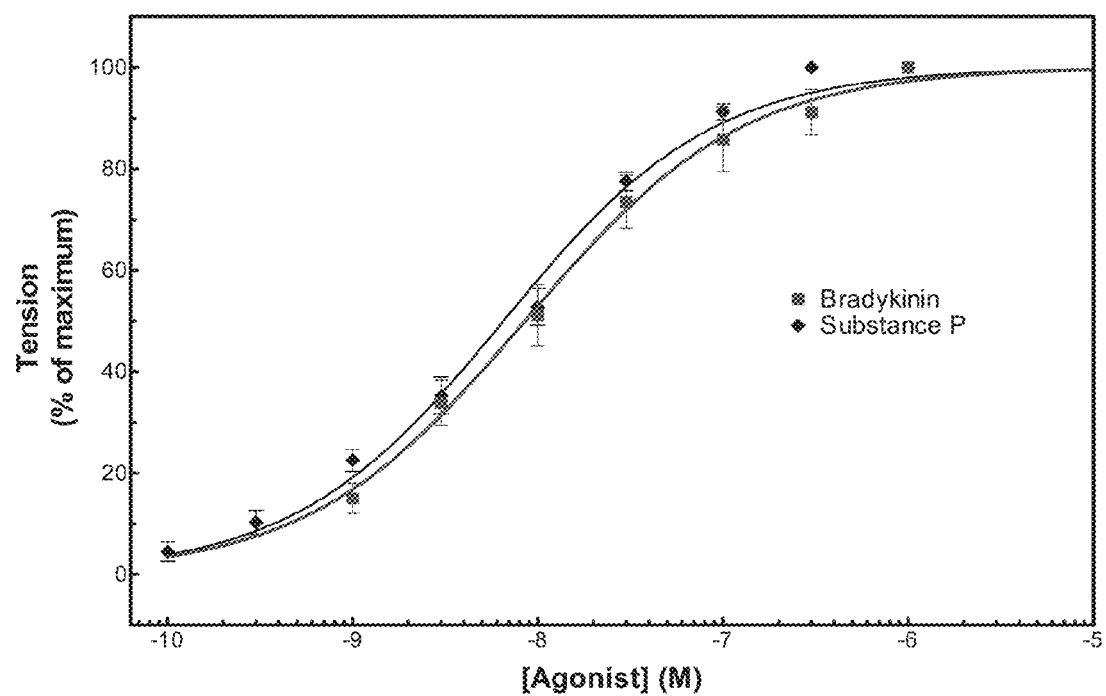
FIG. 2 illustrates the bradykinin and substance P cumulative concentration-response curves obtained from normal animals in Example I.

FIG. 2 illustrates the cumulative concentration-response curves of normal animals to the agonists bradykinin and SP. The $EC_{50}$ for bradykinin was 8.5 nM and for SP was 6.5 nM. This provided a validated system for testing the effects of the inhibitory activity of NSAIDs (COX inhibitors).

Figure 3A:
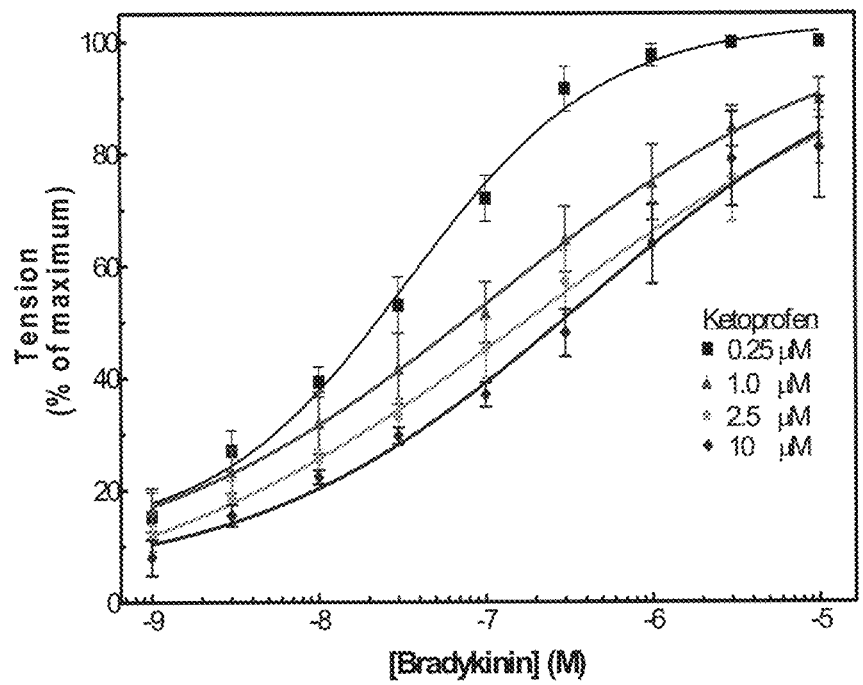
FIG. 3A illustrates bradykinin concentration-response curves produced in the presence of 0.25, 1.0, 2.5 and 10 μM ketoprofen from Example I.
Figure 3B:
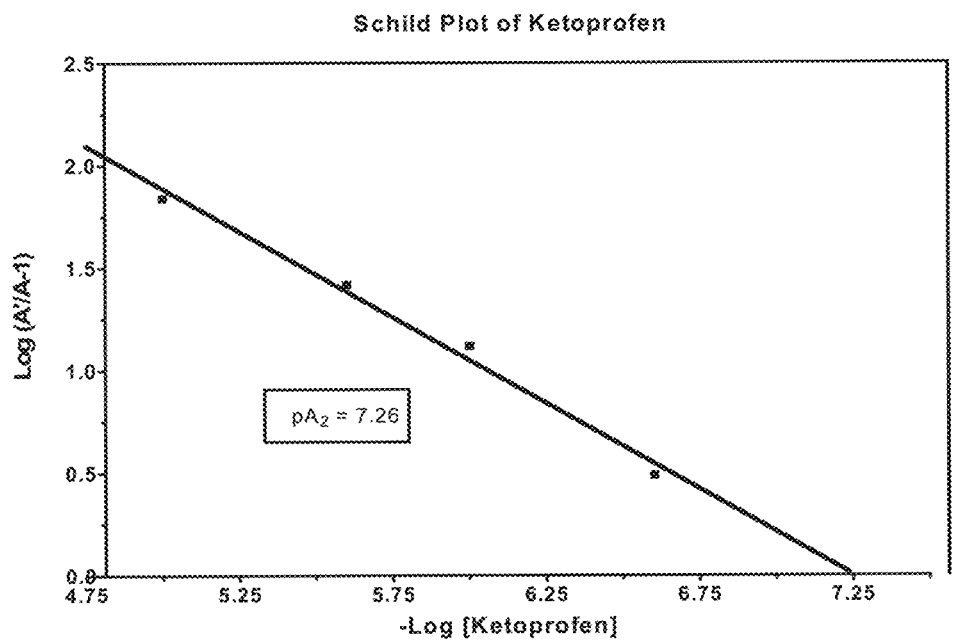
FIG. 3B illustrates the Schild plot for pA2 analysis of ketoprofen from Example I.

FIG. 3A illustrates bradykinin concentration-response curves produced in the presence of 0.25, 1.0, 2.5 and 10 µM ketoprofen. The maximal agonist response could not be determined experimentally for all concentrations of ketoprofen, although curve-fitting using a standard Hill equation revealed no change in maximal response at saturating agonist concentrations. Schild analysis was used to calculate the $pA_2$ value of 7.26 for ketoprofen, equivalent to a $K_D$ for ketoprofen at its site of action of $5.52 \times 10^{-8}$ M (see FIG. 3B). This finding demonstrates that the potency for inhibition in this tissue assay system is quite comparable to values obtained from direct enzyme inhibition assays.

3. $PGE_2$ Determination

Methods

The release of $PGE_2$ from urinary bladder strips into 10 ml of tissue bath was measured using a specific enzyme immunoassay (EIA) according to the manufacturer's instructions (Amersham Pharmacia Biotech) for the basal, bradykinin-induced and COX inhibitor treatment plus bradykinin-induced samples. The COX inhibitors tested were ketoprofen, flurbiprofen, 5-bromo-2-(4-fluorophenyl)-3-(4-methylsulfonyl) thiophene (i.e., DUP-697) and 1-[(4-methysufonyl)phenyl]-3-tri-fluoromethyl-5-(4-fluorophenyl)pyrazole (i.e., SC-58125). One mL of fluid was collected from the 10 mL tissue bath after 10 minutes of bradykinin challenge for $PGE_2$ determination. Samples were frozen immediately and stored at −4° C. until assay. The bladder strips were dried gently by blotting and were then weighed. Results are expressed as picograms of $PGE_2$ released per milligram tissue.

Results

Figure 4A:
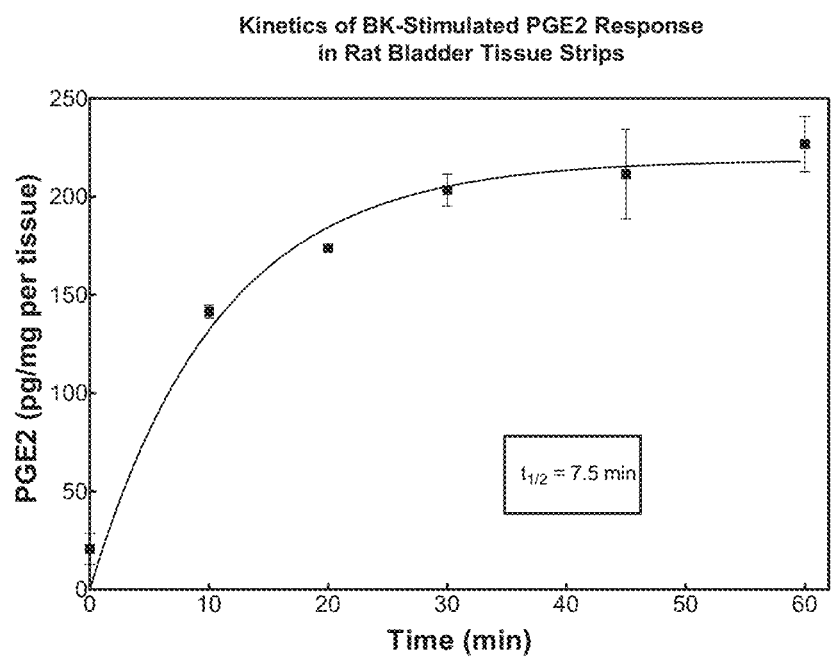
FIG. 4A demonstrates that bradykinin rapidly induces the formation of $PGE_2$ in rat bladder tissue strips tested in Example I within the first minutes of stimulation and reaches a maximum within 30 minutes, with a $t_{1/2}$ for formation of about 7.5 minutes.
Figure 4B:
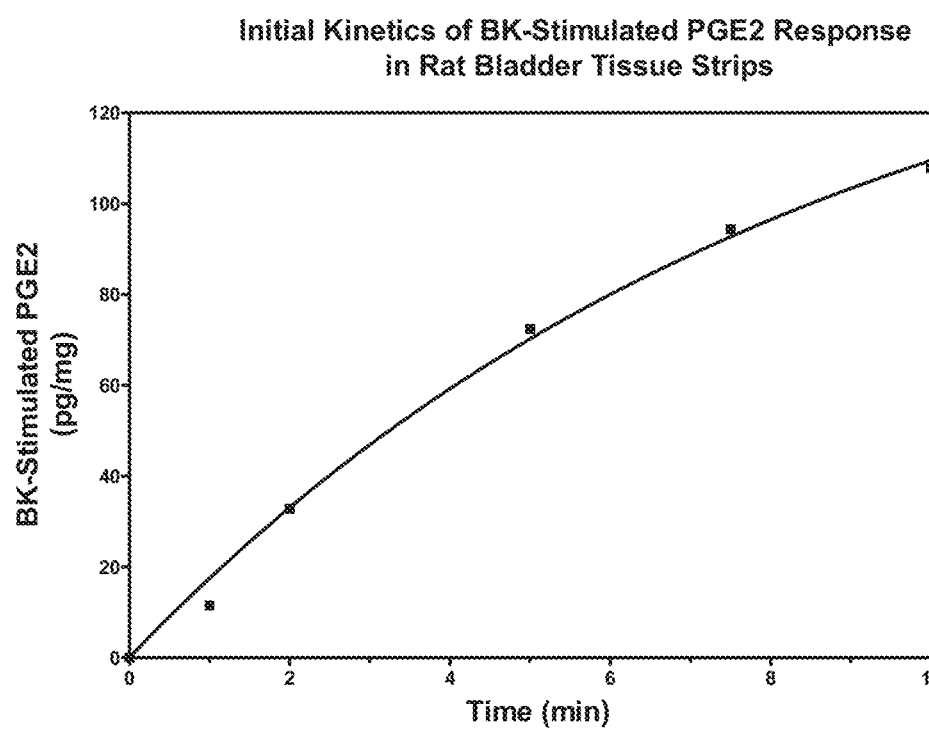
FIG. 4B illustrates the rapid kinetics of $PGE_2$ formation detected within minutes in Example I.

FIG. 4A illustrates that bradykinin rapidly induces the formation of $PGE_2$ in rat bladder tissue strips within the first minutes of stimulation and reaches a maximum within 30 minutes. The $t_{1/2}$ for formation was about 7.5 minutes. FIG. 4B illustrates the rapid kinetics of $PGE_2$ formation detected within the first ten minutes.

Ketoprofen inhibition of bradykinin-induced bladder strip contraction was closely correlated with inhibition of $PGE_2$ formation, as shown in Table 2. Non-selective COX-1/COX-2 inhibitors were found to be effective in blocking bradykinin-stimulated $PGE_2$, while COX-2 selective agents were not effective. This corresponds to a lack of COX-2 inhibitor activity under bradykinin-induced normal cystometry parameters.

TABLE 2

Inhibition of Bradykinin (BK)-induced Contraction with COX Inhibitors

| Drug | BK-induced Contraction IC50 (µM) | BK-induced $PGE_2$ IC50 (µM) |
|---|---|---|
| Ketoprofen | 0.97 | 0.58 |
| Flurbiprofen | 24.8 | 1.65 |
| DUP-697 | >25 | >25 |
| SC-58125 | >25 | >25 |

FIG. 1 (described previously) provides a model for action of prostaglandin activity. Activation of bradykinin receptors on urothelial cells may produce PGs in the urothelium, which in turn may activate bladder nerves (C-fiber and Aδ fibers) to affect bladder contractility and control micturition reflexes. Ketoprofen inhibits formation of $PGE_2$.

4. In Vivo Rat Cystometry Model

Methods

The rats were anesthetized with urethane at 1.2 g/kg i.p. in 5 ml/kg. A polyethylene catheter (PE50) was implanted into the bladder for saline or acetic acid infusion through a 3-way stopcock. A pressure transducer was connected for measurements of intravesical pressure. Warm (37° C.) saline was infused into the bladder at a constant rate of 16.7 ml/min (1 ml/hour) until cystometry became stable (no less than 60 minutes). Thereafter, 0.2% acetic acid was infused into the urinary bladder. Aspirin (10 mg/kg i.v.) and vehicle were administered intravenously via a PE-10 catheter in the femoral vein at 5 minutes after infusion of acetic acid was started and at the end of first micturition cycle. Dunnett's test was applied for comparison between the time before and after test substance or vehicle treatment. To ascertain differences between the test substance and the vehicle control group, an unpaired Student's t test was used. Differences are considered significant at $p<0.5$.

Results

Figure 5A:
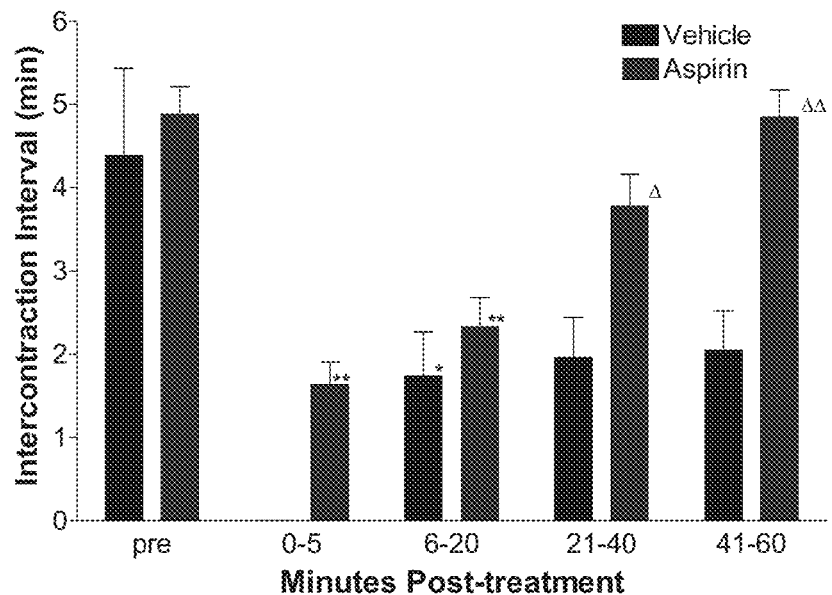
FIG. 5A illustrates that intravenous aspirin (10 mg/kg) produced a gradual time-dependent inhibition of the acetic acid induced reduction in the intercontraction interval (ICI)
Figure 5B:
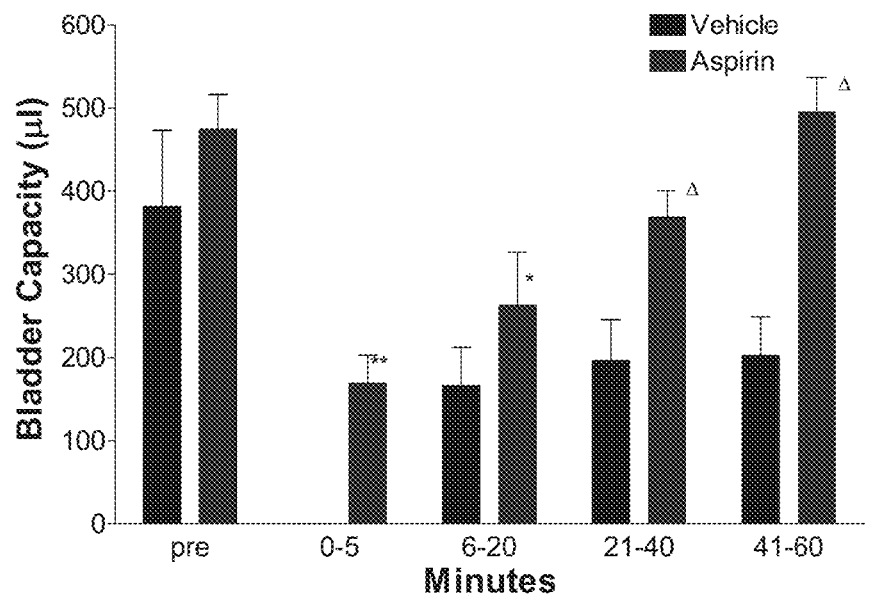
FIG. 5B illustrates the parallel changes in bladder capacity, from Example I.

FIG. 5A illustrates that intravenous aspirin (10 mg/kg) produced a gradual time-dependent inhibition of the acetic acid induced reduction in the intercontraction interval (ICI), and FIG. 5B illustrates the parallel changes in bladder capacity. Threshold pressure and micturition pressure were not affected by aspirin treatment (data not shown).

6. Discussion

These studies demonstrate that $PGE_2$ is rapidly produced in rat bladder tissue following stimulation with bradykinin and that its formation is inhibited by a 10 minute pre-incubation with ketoprofen. Non-selective COX-1/COX-2 inhibitors were demonstrated simultaneously to have blocked the rapid production of PGs in bladder tissue and tissue contractility. Aspirin and other non-selective COX-1/COX-2 inhibitors effectively inhibited cystometric changes induced by intravesical acetic acid stimulation. These studies suggest that delivery of ketoprofen to the urinary tract may be therapeutically beneficial for periprocedural bladder hyperactivity.

Example II

Effects of Ketoprofen and Nifedipine Individually on Bradykinin Induced Contractility in Rat Bladder Tissue Strips The purpose of this study was to characterize the effects of ketoprofen, a non-selective COX-1/COX-2 inhibitor, and nifedipine, an L-type $Ca^{2+}$ channel antagonist, on agonist-stimulated rat bladder contractility using bradykinin as a stimulating agonist.

1. Methods

Ketoprofen USP and nifedipine USP were dissolved in DMSO prior to dilution to the final concentration. Bladder tissue strips from Wistar derived rats were prepared, transduced and equilibrated using the bladder strip contractility method described in Example I above. Assayed tissue was incubated with the test drugs for 10 minutes before activities were determined.

A cumulative contraction-response curve to bradykinin was generated through application of 7 bradykinin concentrations in 3-fold increments ranging from 0.001 to 1 µM at 1 minute intervals for a total of 7 minutes to establish the maximal 100% control response. The tissue was subsequently washed periodically until tension returned to baseline value. In 24 separate tissues, similar bradykinin concentration-responses were carried out in the presence of each respective test compound (ketoprofen: 0.25 µM, 1 µM, 2.5 µM and 10 µM; nifedipine: 0.125 µM, 0.5 µM, 1.25 µM and 5 µM) following a 10 min incubation period. Tissue strips were always used in pairs for the study of the action of the antagonist (bradykinin) alone and in the presence of a concentration of antagonist (ketoprofen or nifedipine). Schild plots were obtained using computer software (Pharmacology Cumulative System, Version 4) and $pA_2$ values were determined.

2. Results

Figure 6:
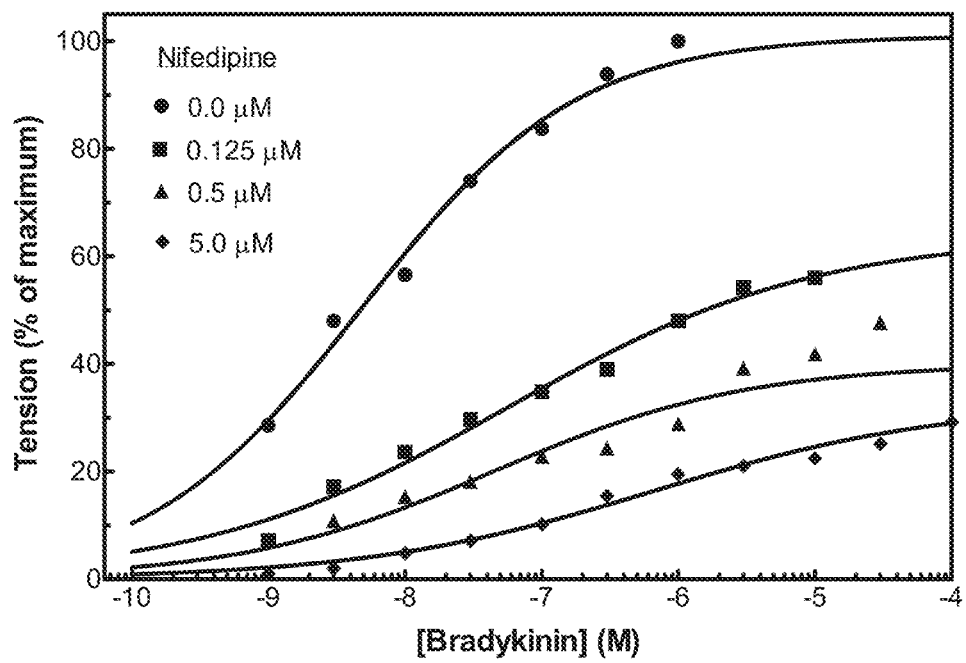
FIG. 6 shows the effect of increasing concentrations of nifedipine on contractility of rat bladder strips from Example II.

Nifedipine was found to exhibit a noncompetitive type of antagonism upon bradykinin-induced contractile responses in the in vitro rat bladder preparation. This was shown by a depression of the maximum agonist response and a small non-parallel rightward shift of the agonist concentration response curves (FIG. 6). In contrast, as previously described in Example I, increasing concentrations of ketoprofen (0.25-10 µM) produced a series of concentration-response curves (see FIG. 3A) in which the $EC_{50}$ agonist response moved progressively to higher concentrations of bradykinin (shift to the right of over 2 orders of magnitude) with no apparent effect on maximal tension. This pattern of inhibition is consistent with a competitive mechanism for ketoprofen and was further analyzed by Schild regression analysis.

For nifedipine, the criteria for application of the Schild regression analysis were not met due to the noncompetitive pattern of inhibition. Even the lowest concentration of nifedipine (0.125 µM) resulted in a large reduction in the agonist response (to about 50% of maximum). These studies of ketoprofen and nifedipine reveal two very different patterns of inhibition of bradykinin-stimulated contractile tension.

Example III

Effects of Ketoprofen and Nifedipine Combination on Bradykinin Induced Contractility in Rat Bladder Tissue Strips The present study evaluated the effects of nifedipine and ketoprofen administered in combination on the contractile tension response in a rat bladder tissue strip model.

1. Methods

Bladder tissue strips from Wistar derived rats were prepared, transduced and equilibrated using the bladder strip contractility method described in Example I above with transduced strips being allowed to equilibrate for 45 minutes. In order to avoid effects of bradykinin receptor desensitization from the cumulative dosing protocol, two tissue strips were collected from each animal. The control group consisted of 12 strips and 54 strips were used for the treatment groups.

Before starting the experiment, each pair of tissue strips was qualified by treating with 0.03 µM bradykinin to determine if the initial difference in maximal contraction between strips was within +/−15%. Following this procedure, qualified tissues were washed repeatedly every 15 minutes for 60 minutes. Cumulative concentration-response curves were generated by application of bradykinin to establish maximal response. For the control group (n=12), a cumulative concentration-response curve to bradykinin was then generated through application of nine concentrations from 0.1 nM to 1.0 µM in 3-fold steps at one minute intervals, for a total of nine minutes to establish the maximal 100% control response. Response curves for the treatment groups involved pre-incubation of the bladder tissue for a period of ten minutes (n=6), followed by generation of bradykinin cumulative dose-response curves by application of 12 concentrations of bradykinin (0.1 nM-30 µM).

The concentration range that was chosen for each of the active agents was based upon results from prior in vitro pharmacological studies of each single agent described in Examples I and II above. Those studies showed that ketoprofen in the 0.3-3 µM range had measurable effects on the $EC_{50}$ for bradykinin activation. Ketoprofen at 3 µM was near maximal in its ability to shift the $EC_{50}$ of the bradykinin activated response curves on muscle contractility. Similarly, prior testing of nifedipine identified a range of concentrations (0.05-5 µM) effective at inhibiting bradykinin induced tension. A factorial design characterized the effects of nine different two-drug combinations of ketoprofen and nifedipine at the following concentrations of (i) ketoprofen: 0.3, 1.0, or 3.0 µM; and (ii) nifedipine: 0.1, 0.3 or 1.0 The treatment groups (groups 2-10) tested are summarized in Table 3 below:

TABLE 3

Ketoprofen-Nifedipine Combinations Tested

| Group | Ketoprofen Conc. (µM) | Nifedipine Conc. (µM) |
| --- | --- | --- |
| 1 (Control) | — | — |
| 2 | 0.3 | 0.1 |
| 3 | 0.3 | 0.3 |
| 4 | 0.3 | 1.0 |
| 5 | 1.0 | 0.1 |
| 6 | 1.0 | 0.3 |
| 7 | 1.0 | 1.0 |
| 8 | 3.0 | 0.1 |
| 9 | 3.0 | 0.3 |
| 10 | 3.0 | 1.0 |

The bradykinin concentration-response data was fit to a variable slope sigmoidal equation, also known as the 3-parameter logistic response (3PL) function, to obtain the maximal tension, $EC_{50}$, and Hill slope in which the bottom of the curve was fixed at 0. The force of contraction in the presence of inhibitors was expressed as a percentage of the maximum bradykinin effects observed within the same strip before addition of an inhibitor.

2. Results

Figure 7:
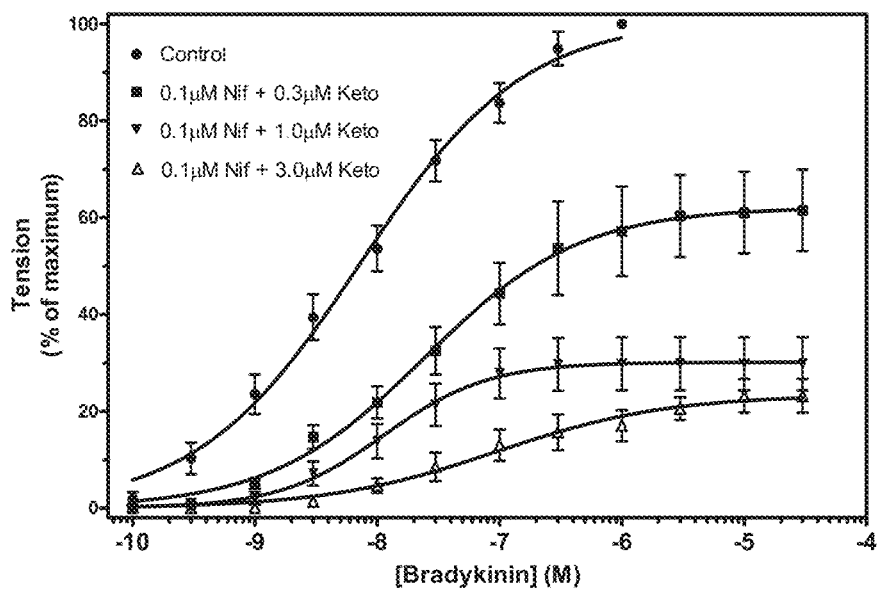
FIG. 7 shows the combined effect of nifedipine (0.1 μM) and ketoprofen (0.3-3.0 μM) on bradykinin-stimulated contractility of rat bladder strips from Example III.

The experimental data for all curves allowed curve fitting to accurately define the maximal tension and $EC_{50}$ values. The control curve in FIG. 7 showed that BK concentration-dependently increased the force of contraction with a $pEC_{50}$ of 8.14 or 72 nM (n=12 strips). A moderate Hill slope of 0.65 characterized the activation curve. All further contraction data was expressed as a percentage of the maximum bradykinin effect obtained from a set of 12 tissue strips without any tension and without any antagonist present.

The results for nine distinct combinations of nifedipine and ketoprofen used to inhibit bradykinin-induced bladder contraction are shown in the following three tables and three figures. At the lowest concentration of nifedipine and ketoprofen tested, 0.1 µM and 0.3 µM respectively, 38% reduction of the maximal control tension was observed (Table 4). Increasing concentrations of ketoprofen (1.0 and 3.0 µM) in the presence of the same concentration of nifedipine further decreased the maximal contractile tension such that only 30 and 23.4% of the control tension remained, respectively. All concentration-response curves for bradykinin shifted to the right in the presence of nifedipine and ketoprofen (0.3-3.0 μM), with the greatest effect seen at the highest ketoprofen concentration. This combination was accompanied by a 1.0 log unit shift in the $pEC_{50}$ versus control. The changes in the $EC_{50}$ parameter did not appear correlated with changes in maximal tension. The results are presented graphically in FIG. 7, which compares the control group and the group having a constant concentration of 0.1 μM nifedipine with a range of concentrations of ketoprofen. The percent of contraction for each drug combination is expressed as the percent of the maximal response for the bradykinin control. The overall pattern of inhibition predominantly reflects a substantial decrease in maximal tension, demonstrating that the combination of nifedipine and ketoprofen act together in combination mechanistically in a non-competitive antagonist manner towards bradykinin-induced contractions.

TABLE 4

Concentration-Response Curve Fitted Parameters for 0.1 μM Nifedipine (NIF) plus 0.3-3.0 μM Ketoprofen (KET)

| Concentration of Drug | $T_{max}$ | | Log $EC_{50}$ | | Hill Slope | |
|---|---|---|---|---|---|---|
| | Est. | SEM | Est. | SEM | Est. | SEM |
| Control | 100.00 | 4.17 | −8.14 | 0.09 | 0.65 | 0.07 |
| 0.1 μM NIF + 0.3 μM KET | 62.11 | 3.90 | −7.61 | 0.18 | 0.69 | 0.16 |
| 0.1 μM NIF + 1.0 μM KET | 30.13 | 1.92 | −7.95 | 0.17 | 1.02 | 0.35 |
| 0.1 μM NIF + 3.0 μM KET | 23.38 | 2.24 | −7.02 | 0.24 | 0.62 | 0.16 |

Est. = Estimated
SEM = Standard error of the mean
$T_{max}$ = Maximal tension determined by curve fitting In the presence of 0.3 μM nifedipine, increasing concentrations of ketoprofen present in the combination treatment resulted in a progressive decrease in the maximal tension, from 36.4 to 16.0%. Combinations utilizing the higher concentration of nifedipine (0.3 μM) resulted in a greater reduction in the maximal tension relative to the corresponding concentrations of ketoprofen in the presence of 0.1 μM nifedipine. The maximal tension levels for 0.3 μM nifedipine combinations were determined for three combinations, in concentration ratios of nifedipine:ketoprofen of 1:1, 1:3.3 and 1:10. The curve fitted parameters data obtained are presented in Table 5.

Figure 8:
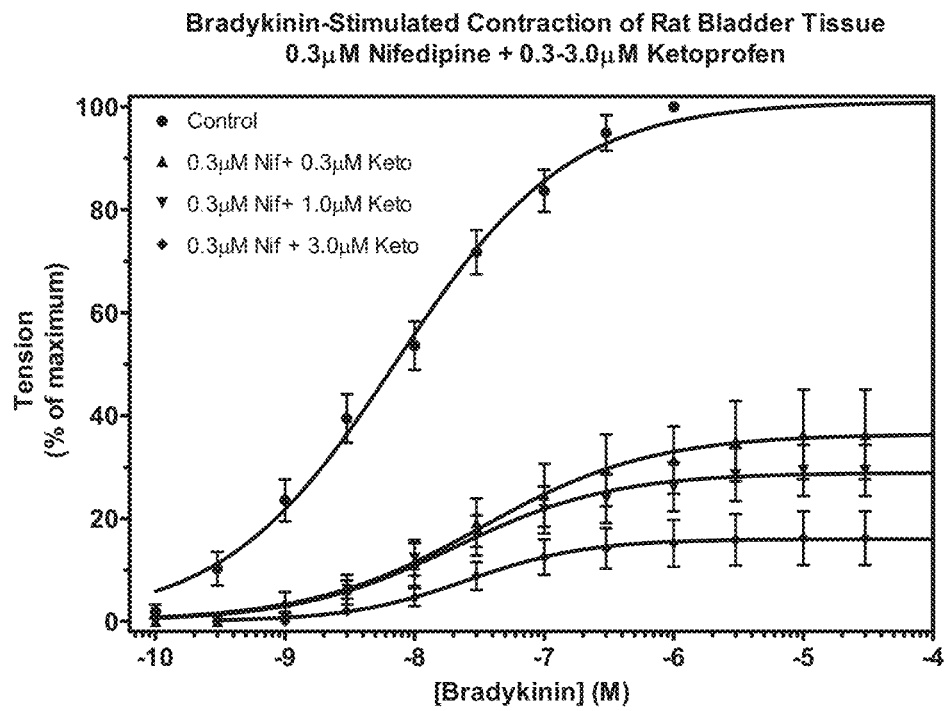
FIG. 8 shows the combined effect of nifedipine (0.3 μM) and ketoprofen (0.3-3.0 μM) on bradykinin-stimulated contractility of rat bladder strips from Example III.

Comparison to data corresponding to ketoprofen concentrations in Table 4 shows that in all cases, greater reductions in the maximal tension were associated with the greater nifedipine concentration. The greatest change was evident at the lowest ketoprofen concentration, 0.3 μM, which decreased from 62.11 to 36.41%. The higher concentrations of ketoprofen resulted in an even greater reduction in tension, such that only 16% remained at 3.0 μM. Associated with these changes in tension, a similar shift in the $EC_{50}$ relative to the control of 0.5 log units was evident for all ketoprofen concentrations at this nifedipine concentration, as can be seen in FIG. 8. As in the case of 0.1 μM nifedipine, no apparent differences between the $EC_{50}$ values for this concentration of nifedipine were evident. Small differences in the Hill slopes for bradykinin agonist responses over the range of inhibitor concentrations were not significant. The effect of increasing ketoprofen concentrations in the combination treatment on the concentration-response curves is similar to the graph of the data at 0.1 μM nifedipine and various ketoprofen concentrations. These graphical data also show the non-competitive nature of the antagonism of the BK-response, which is seen for the combination at this higher concentration of nifedipine.

TABLE 5

Concentration-Response Curve Fitted Parameters for 0.3 μM Nifedipine (NIF) plus 0.3-3.0 μM Ketoprofen (KET)

| Concentration of Drug | $T_{max}$ | | Log $EC_{50}$ | | Hill Slope | |
|---|---|---|---|---|---|---|
| | Est. | SEM | Est. | SEM | Est. | SEM |
| Control | 100.00 | 4.17 | −8.14 | 0.09 | 0.65 | 0.07 |
| 0.3 μM NIF + 0.3 μM KET | 36.41 | 3.84 | −7.49 | 0.29 | 0.66 | 0.24 |
| 0.3 μM NIF + 1.0 μM KET | 28.88 | 2.24 | −7.69 | 0.22 | 0.72 | 0.21 |
| 0.3 μM NIF + 3.0 μM KET | 15.96 | 1.82 | −7.59 | 0.29 | 0.94 | 0.51 |

Figure 9:
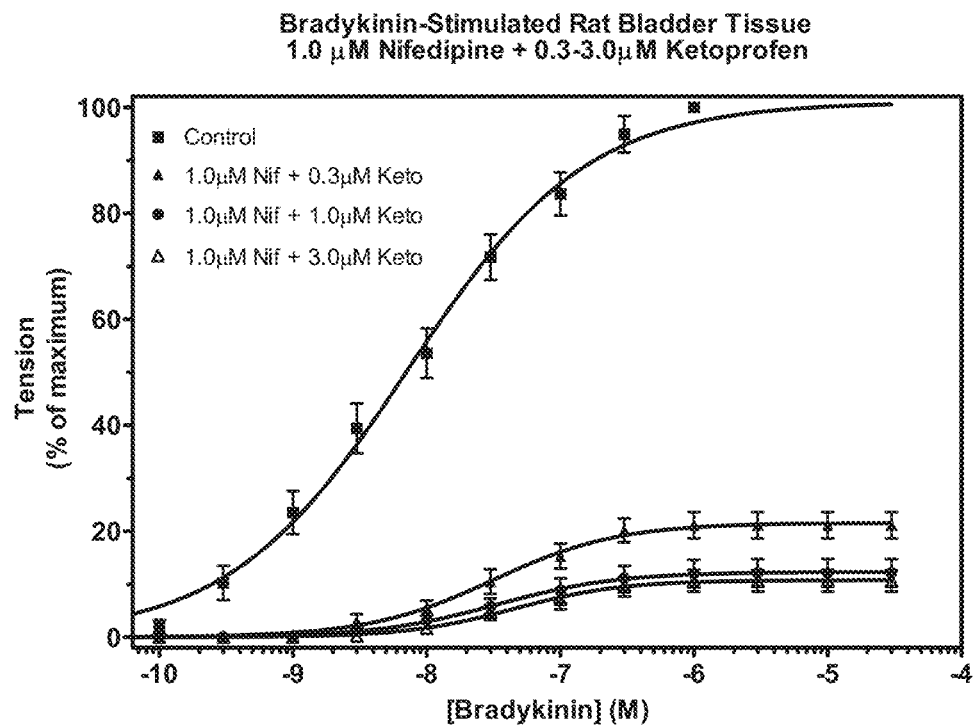
FIG. 9 shows the combined effect of nifedipine (1.0 μM) and ketoprofen (0.3-3.0 μM) on bradykinin-stimulated contractility of rat bladder strips from Example III.

Est. = Estimated
SEM = Standard error of the mean
$T_{max}$ = Maximal tension determined by curve fitting The overall shapes of the response curves observed in the presence of 1.0 μM nifedipine were similar at all concentrations of ketoprofen. At 1.0 μM nifedipine, the maximal tension levels were less than the corresponding values for 0.3 μM nifedipine (Table 6 and FIG. 9), and the magnitude of the additional change due to the presence of ketoprofen is less relative to lower concentrations of nifedipine. The $EC_{50}$ values were uniformly shifted about 0.51 units for all ketoprofen concentrations and were not correlated with maximal tension. This pattern was consistent with observations at all other combination concentrations. A small additional increase in the inhibition of maximal tension due to the change from 1.0 to 3.0 μM ketoprofen was observed at this highest concentration of nifedipine. At the highest concentrations (1.0 μM nifedipine plus 3.0 μM ketoprofen), 89% inhibition of the control tension level was achieved.

TABLE 6

Concentration-Response Curve Fitted Parameters for 1.0 μM Nifedipine (NIF) plus 0.3-3.0 μM Ketoprofen (KET)

| Concentration of Drug | $T_{max}$ | | Log $EC_{50}$ | | Hill Slope | |
|---|---|---|---|---|---|---|
| | Est. | SEM | Est. | SEM | Est. | SEM |
| Control | 100.00 | 4.20 | −8.14 | 0.09 | 0.65 | 0.07 |
| 1.0 μM NIF + 0.3 μM KET | 21.60 | 1.00 | −7.50 | 0.12 | 0.93 | 0.20 |
| 1.0 μM NIF + 1.0 μM KET | 12.30 | 1.00 | −7.48 | 0.20 | 0.96 | 0.35 |
| 1.0 μM NIF + 3.0 μM KET | 10.80 | 0.80 | −7.34 | 0.16 | 1.08 | 0.37 |

Est. = Estimated
SEM = Standard error of the mean
$T_{max}$ = Maximal tension determined by curve fitting 3. Response Surface Analysis The concentrations of the two agents (nifedipine and ketoprofen) used in this combination experiment represent independent variables. The maximal tension is an effect that results from the combination and is the response variable of primary interest for the response surface analysis. The relationship between the drug combinations and the response variable can be represented in a three-dimensional plot in which the concentrations are plotted as Cartesian coordinates in the x-y-plane, and the response variable (e.g., maximal tension) is plotted as the vertical distance above the planar point. The collection of spatial points plotted in this way provides a view that represents the combined concentration-response relationship. The advantages of this experimental design method include the fact that the biological response measured is not limited to a specific response (effect) level of the system. In this way, a number of fixed-ratio concentration combinations can be tested over a wide range of concentrations to define the interaction efficacy of the two drugs.

As in the case of single drug concentration-biological effect relationships in which a smooth curve (or line) may be best fit to the data according to a specific model, a smooth surface may be fit to the data in a three-dimensional plot of a two-drug combination concentration-response relationship. This surface represents the additivity or interaction of the combination. The graph of this response surface becomes the reference surface for viewing actual combination effects and allows the visualization and prediction of effects in regions of the curve for which no data could be generated.

Figure 10:
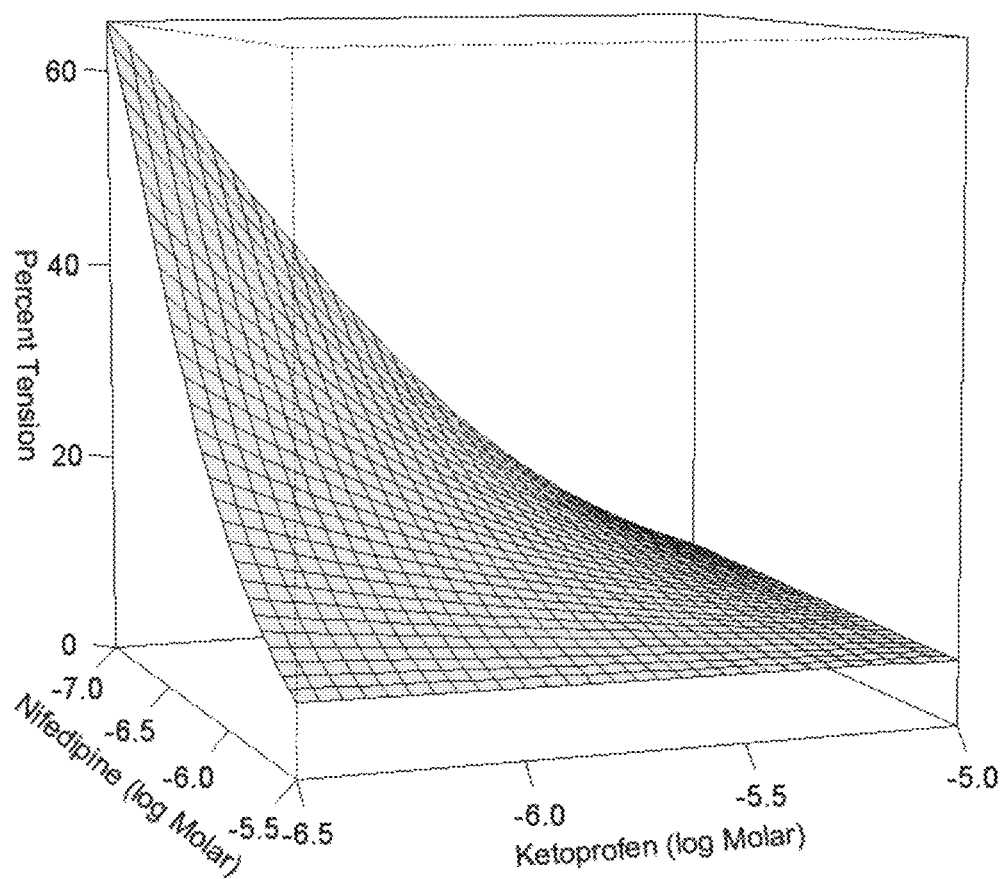
FIG. 10 illustrates the concentration-response surface (reduced model) of individual tension values from dose response curves corresponding to 30 μM bradykinin-induced tension in rat bladder strips from Example III.

A standard response surface analysis was performed on the estimated maximal tension and $EC_{50}$ values. The response surface model was fitted using as a response variable the tension values at the highest agonist concentration on each individual dose response curve, which was the tension corresponding to 30 µM BK. FIG. 10 shows the fitted response surface for the reduced model as a function of ketoprofen and nifedipine concentration. The combination response curve drops steeply with increasing concentrations of both ketoprofen and nifedipine. The surface becomes fairly flat as the maximal response is obtained as concentrations approach 1 µM nifedipine+3 µM ketoprofen. The concentration combination that results in 90% maximal inhibition of the effect of bradykinin is 3 µM of ketoprofen+1 µM of nifedipine.

4. Discussion

The study of this Example III evaluated the effects of nifedipine in combination with ketoprofen using bradykinin as an agonist to stimulate smooth muscle contraction. Bradykinin was used in the rat bladder tissue strip assay system (Examples I-III) to serve as an endogenous mediator of contraction. The overall pattern of inhibition seen with all combinations of nifedipine and ketoprofen concentrations was characteristic of non-competitive antagonism. Nifedipine, which prevents the influx of calcium ions through the cell membrane by acting on L-type voltage-dependent channels, attenuates the bradykinin receptor activated contraction of smooth muscle without directly inhibiting the receptor. As a single agent, nifedipine inhibition was shown above (Example II) to cause a reduction in the maximum bradykinin responses that were not accompanied by statistically significant changes in the agonist potency of the remaining response.

This study revealed the surprising finding that the magnitude of the inhibition is greatly enhanced by the addition of ketoprofen at the lowest nifedipine concentration tested and is evident at all concentrations of the combinations tested. At low concentrations of nifedipine, this inhibition is more than additive, i.e., synergistic in nature. In contrast, ketoprofen treatment alone at the same concentrations was observed to not decrease maximal contractile tension, with no significant effect on the EC50 values for the nine combinations and no concentration dependence upon ketoprofen. Thus, this synergistic interaction on maximal tension and lack of strong effect upon the EC50 was an unexpected result based on the study of ketoprofen action when tested as a single agent in this test system.

Taken together, these data indicate that the effects of the proinflammatory agonist, bradykinin, can be in part mediated by the simultaneous activation of L-type calcium channels and the induction of arachidonic metabolites that together augment smooth muscle contraction. While not wishing to be limited by theory, this effect may be due to a positive feedback loop that operates at a cellular and tissue level. Prostaglandins generated intracellularly as a result of bradykinin receptor activation may move to the extracellular environment, where they may interact and in turn activate prostanoid receptors subtypes. There are at least four known prostanoid receptor subtypes, termed EP1, EP2, EP3 and EP4. Of these subtypes, EP1 receptors are believed to be coupled through G proteins to stimulation of phophoinositide hydrolysis and/or PLC-independent influx of calcium. EP1 receptors have been previously identified in smooth muscle, where they can function to mediate contractile activity. Hence, the discovery of the combined synergistic actions of ketoprofen and nifedipine on contractile activity may be a result of simultaneous blockade of calcium mobilization and the concurrent inhibition of a positive-feedback loop involving $PGE_2$ driven activation of prostanoid receptors.

In conclusion, each combination of nifedipine and ketoprofen showed a greater inhibition of maximal bradykinin-induced contraction compared to either drug alone in the rat bladder tissue strip assay. Furthermore, the multiple combinations of nifedipine and ketoprofen tested allowed a response surface analysis to define optimal concentrations. A fixed ratio combination containing 3.0 µM ketoprofen and 1.0 µM nifedipine was identified that produced ~90% inhibition.

Example IV

Inhibition by Nifedipine and Ketoprofen of Multiple Agonist-Induced Contractile Tension and Release of $PGE_2$ in Rat Bladder Tissue The objective of this study was to evaluate the effects of ketoprofen and nifedipine on rat bladder contractility and agonist-stimulated $PGE_2$ production using multiple agonists. Bradykinin, substance P, histamine and ATP are endogenous mediators that can be released as part of the acute inflammatory response and activate bradykinin receptors (B1 and B2 subtypes), tachykinin receptors ($NK_{1-3}$) and histamine receptors (all subtypes) and purinergic P2X and P2Y receptors, respectively. Carbamylcholine is an agonist that may activate muscle and neuronal nicotinic acetylcholine subtypes or muscarinic acetylcholine receptors subtypes ($M_{1-5}$) present in the bladder, while methoxamine is specific for $\alpha_1$-adrenergic receptors. The first objective was to evaluate the effect of ketoprofen (10 µM) and nifedipine (1 µM) individually, each at a fixed concentration, on contractile tension induced by each of the six agonists (bradykinin, substance P, carbamylcholine, methoxamine, histamine and ATP) in the rat bladder tissue strip model. The second objective was to determine the amount of $PGE_2$ released from the bladder tissue in response to stimulation by each agonist in the presence of either ketoprofen or nifedipine during the same test conditions employed to measure contractile smooth muscle tension.

1. Methods

Bladder tissue strips from Wistar derived rats were prepared, transduced and equilibrated using the bladder strip contractility method described in Example I above. Either 10 µM ketoprofen or 1.0 µM nifedipine was pre-incubated individually with the tissue for a period of 10 minutes prior to stimulation with the following agonists at a concentration equivalent to its respective $ED_{75}$ for stimulation of tension: 0.03 µM bradykinin; 0.03 µM substance P; 3.0 µM carbochol; 30 µM methoxamine; 25 µM histamine; and 20 µM ATP. Antagonist activity for a given concentration of an antagonist (nifedipine or ketoprofen) was determined as the ability of that concentration of the antagonist to reduce the noted agonist-induced (e.g., 0.03 µM bradykinin-induced) response by 50 percent or more (50%). Each concentration of antagonist was tested in four separate tissue preparations.

The effects of the two drugs on $PGE_2$ release in response to multiple agonists was compared using the same 10 min pre-incubation protocol and a subsequent 30 min incubation period with agonist in the presence of the test compound. $PGE_2$ produced after 30 minutes of treatment with each agonist (e.g., 0.03 µM bradykinin) in the absence and presence of the test compounds was determined. An initial 1.0 ml sample was taken from the tissue bath after a 30 minute incubation with the agonist. Subsequently, the tissue was washed using 10 ml of Krebs solution every 15 minutes for a 2 hour period. The test compound was added and pre-incubated for a period of 10 minutes prior to re-challenge with the same agonist. After an additional 30 minute period in the presence of the test antagonist and agonist, 1.0 ml was removed from the bath for analysis. The release of $PGE_2$ from urinary bladder strips was measured using a specific enzyme immunoassay (EIA). Samples were frozen immediately and stored at −4° C. until assay. The bladder strips were dried gently by blotting, and then weighed. Results are expressed as picograms of $PGE_2$ released per milligram tissue.

2. Results

Figure 11:
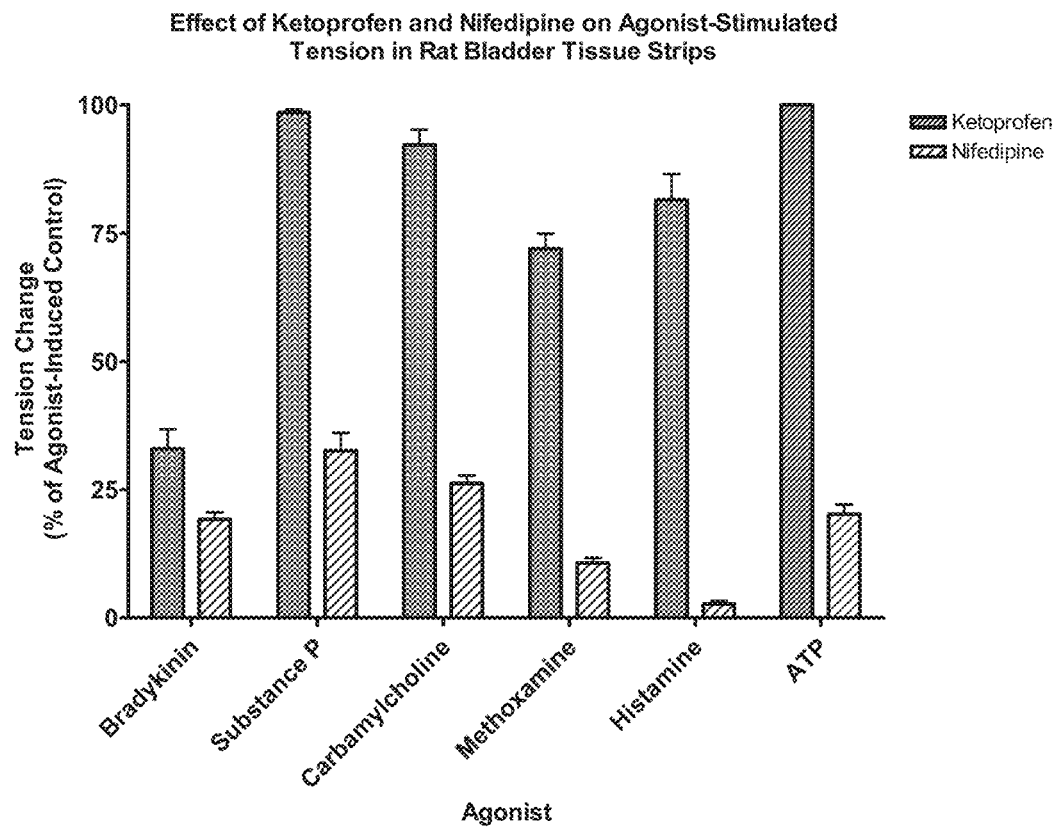
FIG. 11 shows the effect of ketoprofen (10 μM) and nifedipine (1 μM), individually, on multiple agonist-stimulated tension in rat bladder tissue strips from Example IV.

All of the agonists investigated stimulated contraction of the bladder tissue strips, independent of their mechanism of action, demonstrating that multiple mediators can increase bladder smooth muscle contractile tension. Nifedipine (1 µM) produced a significant inhibition (>67%) of each agonist-induced increase in contractile tension (FIG. 11). The contractile response to bradykinin was affected by both nifedipine and ketoprofen (81% inhibition and 67% inhibition, respectively). In contrast, the increase in contractile tension induced by substance P, carbamylcholine and ATP was not affected by ketoprofen. Ketoprofen also only slightly reduced the tension for methoxamine and histamine (<25%).

Figure 12:
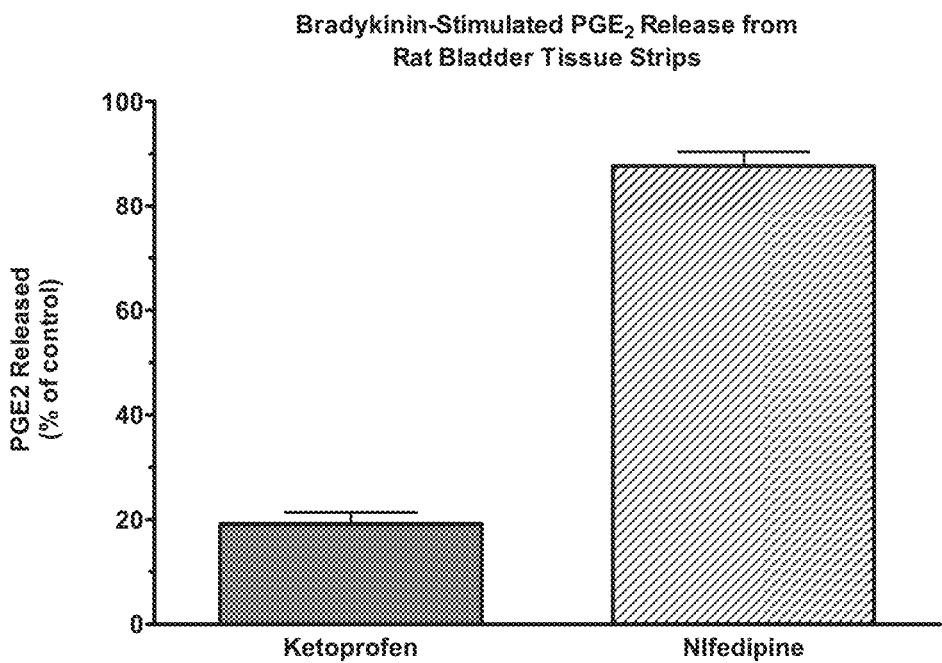
FIG. 12 shows the effect of ketoprofen (10 μM) and nifedipine (1 μM), individually, on bradykinin-stimulated $PGE_2$ release from rat bladder tissue strips from Example IV.

Bradykinin evoked the largest increase in $PGE_2$ relative to the other agonists tested. This evoked release was effectively inhibited by ketoprofen (81%) but minimally affected by pre-treatment with nifedipine (12%) (FIG. 12). Thus, the extent of inhibition of smooth muscle tension by nifedipine was not linked to agonist-induced $PGE_2$ responses and was distinct from the effect of ketoprofen. The absolute bladder levels of $PGE_2$ produced in response to stimulation by other GPCR agonists were about 10-fold less than those seen with bradykinin.

In summary, the current study indicated that an increase in smooth muscle contractile tension can be induced by a variety of GPCR agonists in bladder tissue. Moreover, a common signaling mechanism for these agents is mediated in part through activation of L-type $Ca^{2+}$ channels in the rat urinary bladder. Nifedipine's inhibition of L-type $Ca^{2+}$ channels suggests an effective mechanism for inhibition of numerous pathophysiological mediators that can lead to increased smooth muscle bladder tension associated with spasm or hyperactivity. Ketoprofen inhibited bradykinin-stimulated $PGE_2$ production and release from the bladder while nifedipine did not exhibit an effect on this response. Thus, nifedipine and ketoprofen act through distinct mechanisms to inhibit smooth muscle contractile tension and release of pro-inflammatory prostaglandins in bladder tissue.

Example V

Effect of Ketoprofen and Nifedipine on Rat Bladder Function in an Acetic-Acid Overactive Bladder Model The primary objective of this study was to measure the effect of ketoprofen and nifedipine during intravesical, local delivery to female rats with overactive bladder function caused by perfusion with saline containing 0.2% acetic acid (acidified saline). Perfusion of 0.2% acetic acid through the bladder is known to rapidly induce an acute inflammatory state that is reflected in functional changes in bladder cystometry.

1. Methods

The method used in the current study represents an adaptation of a widely used acetic acid-triggered rat model of hyperactive bladder. In this model, acute inflammation of the bladder is produced by using 0.2% acetic acid in saline as the bladder perfusion fluid and cystometry under anesthesia is performed after a recovery period from the surgical procedure. A regular interval of voiding cycles can be seen for several hours after the initial stabilization period occurs. A bladder catheter connected to an infusion pump was used to deliver the drug solutions directly to the bladder at a constant, defined rate.

The animals were anesthesized and bladder catheters were surgically implanted to allow irrigation of the test agents. The following cystometry parameters were monitored: inter-contraction interval (ICI), trigger pressure (TP), micturition pressure (MP) and micturition volume (MV) using a Med Associates Cystometry Station and software program. Only rats that displayed normal and stable cystometry profiles during the preliminary saline-infusion stage (not less than 15 min of baseline stabilization followed by 7 regular representative ICI intervals) were included in the study. Following the saline period, the rat bladder was infused with test agent in saline containing 0.2% acetic acid for 20 min followed by the collection of 7 representative ICI intervals for analysis. Due to the fixed concentrations of the irrigation solutions employed in the study and the use of constant perfusion rates for fixed constant times, a fixed, uniform dose of each agent was delivered to all animals.

Groups of female rats were administered ketoprofen at selected concentrations (0.01-25 µM) alone or nifedipine at selected concentrations (0.1-10 µM) alone. Five to seven animals were normally tested in each group. Acidified saline served as the control. All infusion solutions were prepared fresh on the day of the experiment before use. For each of the test agents, three distinct bladder irrigation periods were employed: 1) baseline (saline only) for 1 hour; 2) drug in saline only for 15 minutes; and 3) drug in 0.2% acidified saline for 1 hour.

2. Results

Figure 13:
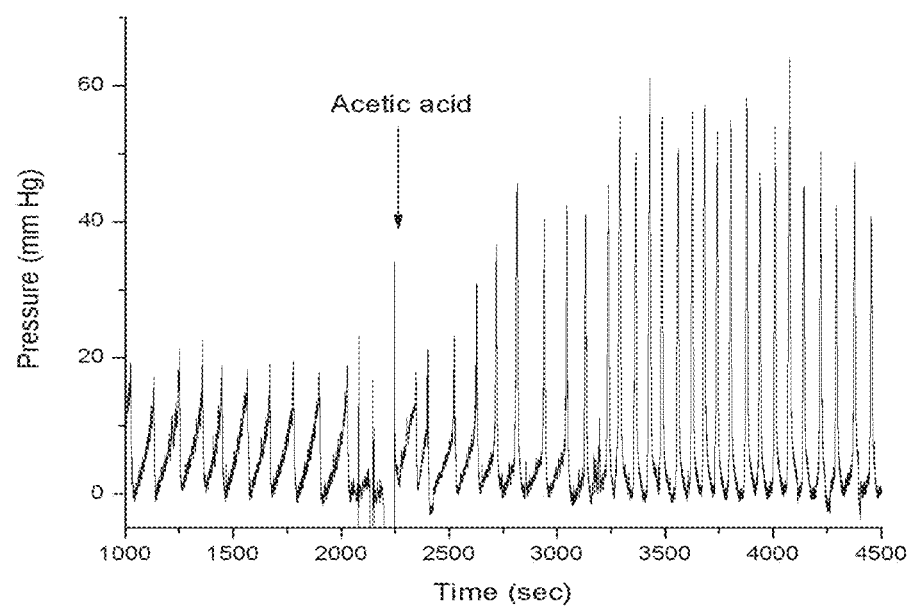
FIG. 13 shows a rat bladder cystometry tracing demonstrating the effect of acetic acid perfused as described in Example V.

In the control animals, baseline levels of bladder contractions in response to a constant irrigation rate of 0.1 µl/min saline were established during the first hour following surgery. The time between contractions (ICI, seconds) and peak micturition pressure (MP, mm Hg) appeared to vary somewhat between animals but was fairly constant within animals following stabilization. Following the addition of the 0.2% acetic acid to the perfusion buffer, rapid contractions appeared, resulting in a significant decrease in the ICI. Increases in contractile pressure accompanied the shortening of time between the bladder contractions in many cases as well. These changes in functional bladder responses could be routinely measured following perfusion of the bladder with acidified saline, as shown in FIG. 13. A 40-50% shortening of the ICI was typically seen in the control group in response to the 0.2% acetic acid irrigation (mean % ICI=58.4%±6.8%, n=8).

Figure 14:
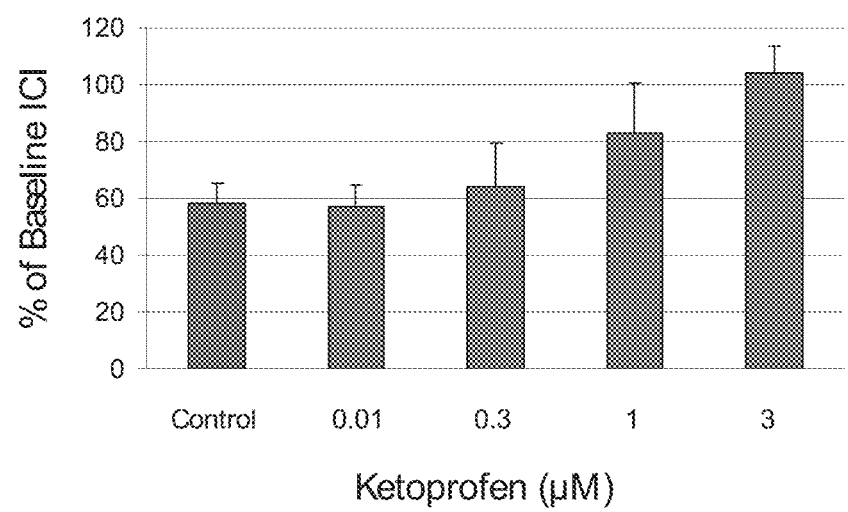
FIG. 14 demonstrates the effect of ketoprofen pretreatment on acetic acid-induced bladder hyperactivity from Example V.

Inclusion of ketoprofen in the irrigation buffer leads to a concentration-dependent inhibition of the shortening of the ICI (FIG. 14). Complete inhibition was seen at approximately 3 µM ketoprofen and higher concentrations tended to go above 100% (data not shown).

Figure 15:
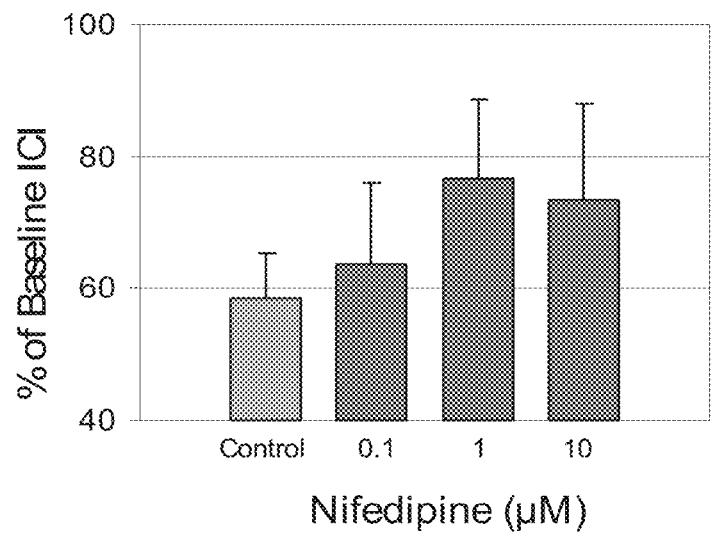
FIG. 15 demonstrates the effect of nifedipine pretreatment on acetic acid-induced bladder hyperactivity from Example V.

Inclusion of nifedipine in the irrigation buffer also leads to a concentration-dependent inhibition of the shortening of the ICI (FIG. 15). Complete inhibition was not seen but maximal effects appeared to be at 1 µM nifedipine, and higher concentrations tended to plateau at approximately 75% of baseline.

Example VI

Pharmacokinetics of Absorption of a Nifedipine and Ketoprofen Combination in a Rat Bladder Saline Model The primary objective of this study was to measure systemic plasma levels of ketoprofen and nifedipine during and after the intravesical, local delivery of a combination of these drugs to rats. A secondary objective of this study was to determine the rate of appearance of ketoprofen and nifedipine when administered individually or in combination. Finally, a third objective of this study was to evaluate the effects of local drug delivery on the rat bladder tissue content of the pro-inflammatory mediator, $PGE_2$, following surgical trauma to the bladder and subsequent intravesical perfusion of each agent or the combination.

1. Methods

The study included three main treatment groups of animals: a combination of both ketoprofen (10 µM) and nifedipine (10 µM); ketoprofen (10 µM) alone; and nifedipine (10 µM) alone. A bladder catheter connected to an infusion pump was used to deliver the drug solutions directly to the bladder at a constant, defined rate.

For each of the three drug treatment groups, three distinct bladder irrigation periods were employed that were defined by the bladder perfusion solution for each period: 1) baseline (saline only) for 1 hour; 2) drug in saline only for 1 hour; and 3) post-drug saline period for 30 minutes (min). The animals were anesthetized and the dome of the bladders were surgically implanted with a catheter to allow perfusion of the test agents with an infusion pump at a constant flow rate of 100 µl/min. During period 1, saline was the perfusion fluid used and no plasma samples were collected. Starting at period 2, plasma samples were collected at time points of 0, 15, 30, 45 and 60 min following perfusion of test agents. Subsequent to 60 min of perfusion with test agents, only saline was perfused for an additional 30 min and two additional time points at t=75 and 90 min were collected to determine the acute post-perfusion phase of test agents. Due to the fixed concentrations of the irrigation solutions employed in the study and the use of constant perfusion rates for fixed constant times, a fixed, uniform dose of each agent was delivered to all animals.

Whole blood samples were collected into $K_2$ EDTA tubes at the specified collection times. The volume of whole blood collected was approximately 0.2 mL per sample. The blood was spun in a centrifuge and the plasma transferred into polypropylene tubes. Plasma samples were stored frozen at −80° C. until shipment for analysis. Rats were euthanized by $CO_2$ inhalation and the bladder was rapidly dissected and frozen in liquid nitrogen and stored frozen at −80° C. until assayed for tissue $PGE_2$ content.

The combination of ketoprofen and nifedipine was formulated in accordance with an aspect of the invention to include ketoprofen (10 mM), and nifedipine (10 mM) in a 60% polyethylene glycol 400 (PEG 400):40% water solvent base, including 50 mM sodium citrate buffer for a pH 7.5 solution in a 5 mL glass vial. Immediately prior to use, the combination solution was diluted in the standard irrigation fluid at a ratio of 1:1000 such that the final concentrations of the active drugs delivered directly to the bladder were each 10 µM. For these experiments, a fixed concentration ratio of 1:1 nifedipine:ketoprofen was chosen, and final concentrations of 10 µM for each agent were maintained in the irrigation buffer.

2. Results

The study demonstrated a very low level of systemic absorption of ketoprofen following perfusion of the bladder with saline containing 10 µM ketoprofen for 60 min. In four out of six rats, a narrow range of $C_{max}$ between 4.3-5.8 ng/ml was seen at 60 min. At the 60 min time point, the perfusion with 10 µM ketoprofen was stopped and normal saline irrigation was continued for an additional 30 min period. For the group of four out of six rats which showed peak plasma levels of about 5 ng/ml, plasma levels decreased at 75 and 90 minutes following cessation of ketoprofen perfusion. Delayed absorption during the 75-90 minute interval was observed in the other two animals in the ketoprofen-only group.

For comparison, the ketoprofen levels were also determined for the combination of ketoprofen and nifedipine. The increase in systemic plasma levels was approximately linear over time during the initial 60 minute drug perfusion phase and the absolute mean plasma levels of 9.3 ng/ml (n=6) at 60 minutes were well below the acceptable therapeutic daily dose of ketoprofen. As in the case of the ketoprofen only group, the perfusion with the combination was stopped and normal saline irrigation was continued for an additional 30 minute period. The mean ketoprofen values for all animals (n=6) were not significantly different at 60, 75 and 90 minutes.

Figure 16:
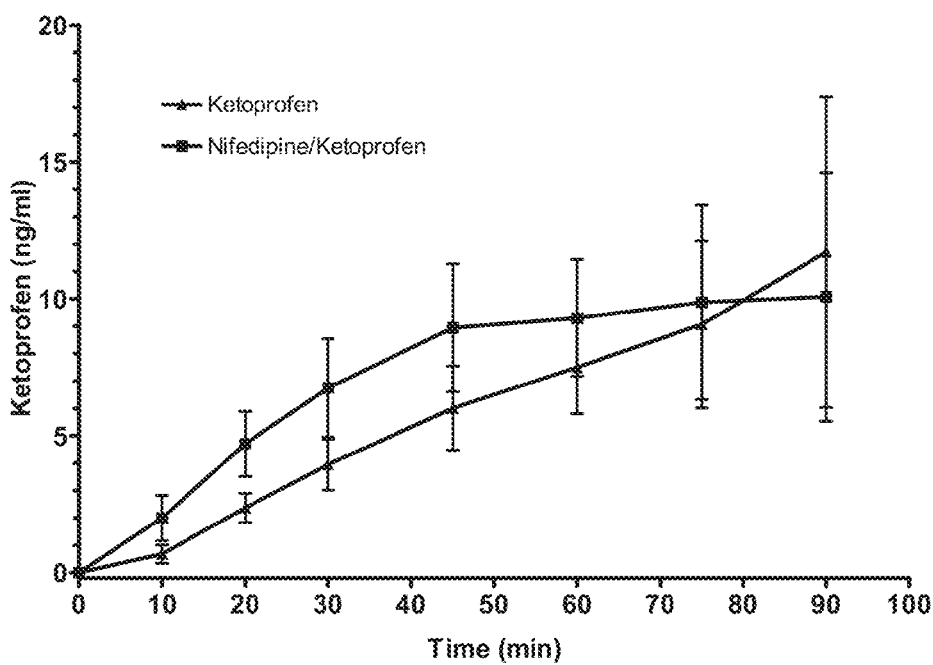
FIG. 16 illustrates mean ketoprofen plasma levels for rats treated with ketoprofen or a combination of ketoprofen and nifedipine in the pharmacokinetic study of Example VI.

A comparison of the mean plasma ketoprofen results are presented graphically in FIG. 16 for the ketoprofen-only group and the combination group. The mean values (and standard error of the means, SEMs) clearly show the constant plasma levels for the combination after 60 minutes. Although small differences are apparent in the earliest phase of the time-course, no significant differences were observed either in the peak levels or in the absorption kinetics for the ketoprofen plasma levels in the combination group versus the ketoprofen alone group after 30 minutes, or in the peak levels, indicating that no apparent ketoprofen-nifedipine drug interactions were present.

The overall kinetic profile observed for nifedipine was similar to that observed for ketoprofen. In the nifedipine-only plasma group, nifedipine plasma levels increased linearly in 5/6 animals and some delayed absorption was observed in only 1/6 animals. The $C_{max}$ plasma level in the nifedipine group was in the range of 10.6-16.0 ng/ml at 60 minutes for 5/6 animals. The mean peak plasma levels observed at 60 minutes were below the acceptable mean peak levels of 79±44 ng/ml that are obtained in man as a result of an oral therapeutic daily dose of nifedipine.

The increase in nifedipine systemic plasma levels from the combination of ketoprofen and nifedipine also exhibited a linear increase with increasing time for the initial 60 minute drug perfusion period. The $C_{max}$ plasma levels in the combination group had a mean value of 18.2 ng/ml and values ranged from 8.2-34.6 ng/ml at 60 minutes for all six animals. The mean peak plasma levels observed at 60 minutes are about one fourth the mean peak levels that are obtained as a result of oral therapeutic daily dose of nifedipine.

Figure 17:
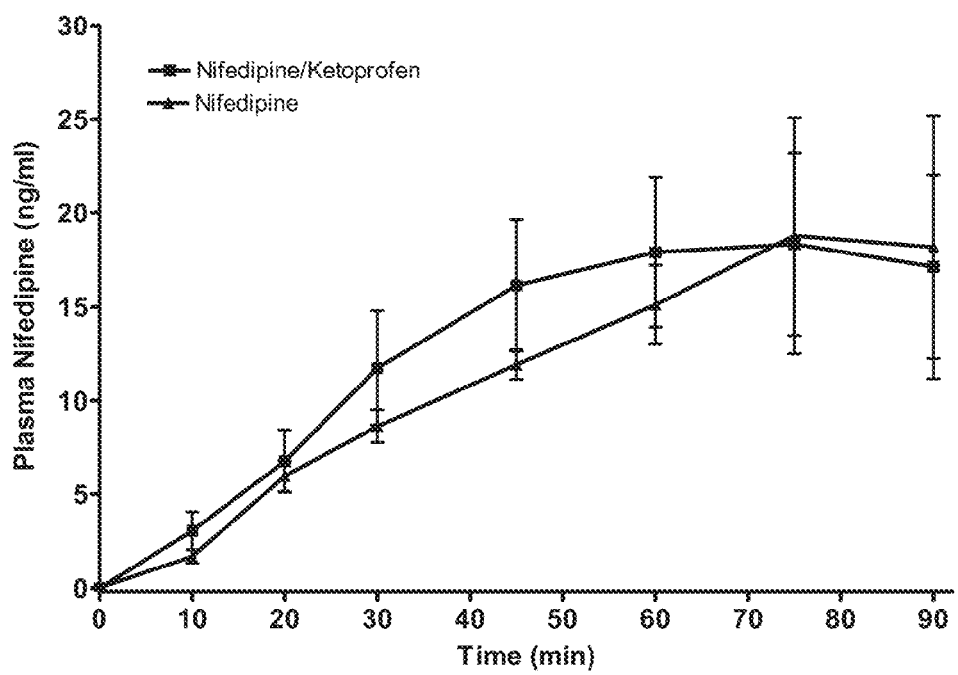
FIG. 17 illustrates mean nifedipine plasma levels for rats treated with nifedipine or a combination of ketoprofen and nifedipine in the pharmacokinetic study of Example VI.

As shown in FIG. 17, a comparison of the mean peak plasma concentrations of nifedipine (and plotted SEMs) shows the similar linear increase that occurs during the initial perfusion phase of intravesical delivery. No significant differences in nifedipine plasma levels were seen in the nifedipine only group when compared with the nifedipine and ketoprofen combination drug product group.

Figure 18:
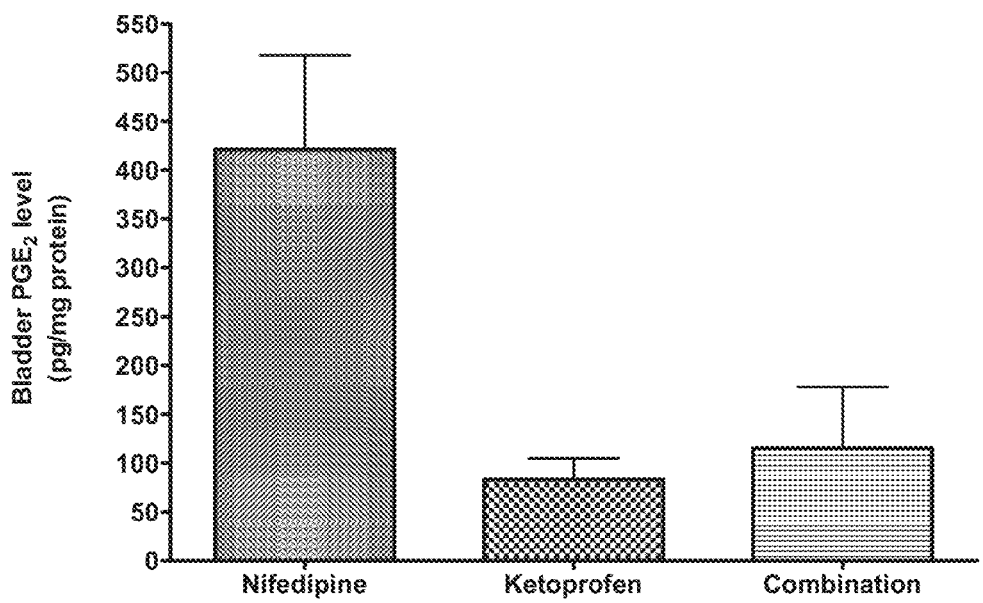
FIG. 18 illustrates the effects of nifedipine, ketoprofen and a combination of nifedipine and ketoprofen on $PGE_2$ in rat bladders from the pharmacokinetic study of Example VI.

At the end of the 90 min bladder perfusion period, bladders were harvested from the animals and subsequently the entire bladder was analyzed for $PGE_2$ content using an enzyme immunoassay system. Data shown in FIG. 18 are expressed as the mean of $PGE_2$ using units of pg/mg protein±the standard error of the mean from six animals per treatment group. When animals were treated with nifedipine, bladder tissue $PGE_2$ levels of 421±97 pg/mg protein (n=6) were observed compared to statistically significantly ($p<0.05$) lower levels in the presence of only ketoprofen or ketoprofen and nifedipine in the combination treatment group, 83±22 (n=6) and 115±63 pg/mg (n=5), respectively. No statistically significant differences were seen between the ketoprofen treatment or the combination treatment groups. In summary, ketoprofen treatment alone or treatment with the combination during bladder perfusion significantly inhibited $PGE_2$ formed in the whole bladder relative to the nifedipine treatment group.

3. Discussion

Using a method of intravesical perfusion for local drug delivery, the drugs tested in this study were directly in contact with the absorptive site within the bladder. The continuous perfusion maintained constant drug concentrations of either ketoprofen, nifedipine or the combination within the bladder during the period of drug delivery. Under these conditions, minimal systemic exposure to the drugs occurred in female rats during a 1 hour intravesical perfusion. Low levels of each drug were detectable within the first 15 min interval measured, and absorption progressed gradually as an approximately linear function over time of drug perfusion for each agent.

The locally delivered drugs and drug combination were exposed to the structures of the bladder, including the uroepithelium, C-fiber afferents, efferents and smooth muscle. The data obtained in the study show that this action is local and cannot be ascribed to systemic effect that could be mediated through central nervous system mechanisms because the initial levels in the plasma for both drugs tested are so low.

Comparison of the plasma levels for each agent tested to known human levels associated with normal oral dosing reveals the magnitude of the difference observed. In the combination treatment group, the maximal levels for ketoprofen were about 400-fold less than the peak plasma levels ($C_{max}$) in humans that are associated with the acceptable therapeutic daily dose of ketoprofen (rat mean ketoprofen plasma level of 9.29±2.13 ng/ml at 60 min). For comparison, the accepted daily mean peak $C_{max}$ for a single 200 mg ketoprofen tablet (a single oral dose) is 3900 ng/ml. Similarly, peak levels observed for nifedipine were approximately 15 ng/ml to 25 ng/ml. The maximal levels ($C_{max}$) typically occurred at the end of 60 min drug perfusion period or within the following 30 min sampling period. For comparison with known plasma levels from conventional oral dosing, the accepted daily $C_{max}$ for a single 10 mg immediate release nifedipine tablet is reported to be 79±44 ng/ml. Systemic exposure was comparable for ketoprofen plasma levels whether administered alone or with nifedipine. Similarly, nifedipine plasma levels were comparable whether administered alone or with ketoprofen.

This study also determined the $PGE_2$ content of the bladder for each of the treatment conditions in the study. An additional finding of significance is the long-lasting effect of ketoprofen that was measured in the assay of whole bladder $PGE_2$ levels. The low concentrations of the ketoprofen treatment alone or the combination treatment during bladder perfusion significantly inhibited $PGE_2$ formed in bladder tissue relative to the nifedipine treatment group. The $PGE_2$ bladder tissue levels in the presence of ketoprofen were not significantly different from those following treatment with the combination. Because delivery of the drug was stopped at 60 minutes in this study, and then saline was used to irrigate for an additional 30 minutes, this showed that $PGE_2$ inhibition remained active in the post-drug delivery period. Thus, ketoprofen demonstrated an extended period of anti-inflammatory activity in this model of local, intravesical drug delivery.

Example VII

The purpose of this study was to evaluate the solubility of ketoprofen and nifedipine in aqueous liquid solution formulations.

1. Methods

Three ketoprofen and nifedipine combo liquid formulations, identified as F3/1, F10/3, and F30/10, were prepared according to the composition shown in Table 8 below. In all three test formulations, 50 mM sodium citrate aqueous buffer was used. The target solubility of ketoprofen/nifidipine for F3/1, F10/3, and F30/10 were 3 mM/1 mM, 10 mM/3 mM, and 30 mM/10 mM respectively.

TABLE 8

Solubility Results for Three Nifedipine and Ketoprofen Combination Formulations

| Formulation ID | Formulation Buffer | PEG400 % (v/v) Added to Buffer | Target Solubility (Ketoprofen/Nifedipine) | Approximate Saturation Solubility (Ketoprofen/Nifedipine) |
|---|---|---|---|---|
| F3/1 | 50 mM Na citrate buffer pH 5.5 | 35% | 3 mM/1 mM | 4.5 mM/1.5 mM |
| F10/3 | 50 mM Na citrate buffer pH 5.5 | 50% | 10 mM/3 mM | 15 mM/4.5 mM |
| F30/10 | 50 mM Na citrate buffer pH 5.5 | 60% | 30 mM/10 mM | 45 mM/15 mM |

2. Results

In order to achieve complete dissolution of both actives, ketoprofen and nifedipine, in the formulations, different percentages of PEG 400, 35% v/v PEG 400 (F3/1), 50% v/v PEG 400 (F10/3), 60% v/v PEG 400 (F30/10), were used as a cosolvent. With the assistance of PEG 400 as a solubilizing agent, the approximate saturation solubility of ketoprofen and nifedipine in all three formulations was approximately 1.5× of their respective target solubility. The solubility results in Table 8 clearly indicate that PEG 400 is a suitable solubility enhancing agent for both drugs when it is desired to prepare highly concentrated combination solution formulations.

Example VIII

The purpose of this study was to evaluate the stability of exemplary combination ketoprofen and nifedipine aqueous liquid solution formulations.

1. Methods

Four exemplary ketoprofen and nifedipine combination solution formulations, identified as F1 to F4, were prepared according to the composition shown in Table 9. In all four formulations, the concentrations of the active drugs were 3 mM for Ketoprofen and 1 mM for Nifedipine. All four formulations employed sodium citrate buffer (pH 5.5) with a 35% v/v of PEG 400. The ionic strength of the buffer used was 50 mM for F1 and F2, and 20 mM for F3 and F4. No antioxidant was added to the virgin formulation F1, while 0.05% propyl gallate, 0.02% sodium metabisulfite, and 0.05% propyl gallate plus 0.02% sodium metabisulfite were added to the combination formulations F2, F3, and F4 respectively.

TABLE 9

Tested Nifedipine and Ketoprofen Combination Formulations

| Formulation ID | Drug Concentration (Ketoprofen/ Nifedipine) | Formulation Vehicle | Antioxidants Added |
|---|---|---|---|
| F1 | 3 mM/1 mM | 50 mM NaCitrate (pH 5.5) w/ 35% v/v PEG 400 | None |
| F2 | 3 mM/1 mM | 50 mM NaCitrate (pH 5.5) w/ 35% v/v PEG 400 | 0.05% Propyl gallate |
| F3 | 3 mM/1 mM | 20 mM NaCitrate (pH 5.5) w/ 35% v/v PEG 400 | 0.02% Sodium metabisulfite |
| F4 | 3 mM/1 mM | 20 mM NaCitrate (pH 5.5) w/ 35% v/v PEG 400 | 0.05% Propyl gallate & 0.02% Sodium metabisulfite |

An isocratic high performance liquid chromatograph (HPLC) method was used to quantify ketoprofen and nifedipine and their related substances in these test solution formulations after storage for different periods of time. Formulation samples were taken and diluted into mobile phase to obtain a final concentration of approximately 0.76 mg/mL to 2.54 mg/mL for ketoprofen and approximately 0.35 mg/mL to about 1.15 mg/mL for nifedipine. Chromatographic conditions for the related substances assay were as follows: (1) detection wave length: UV 241 nm; (2) column: Zorbax SB-C18, 5 µM, 4.6×150 mm; (3) column temperature: 30±1° C.; (4) flow rate: 1.0 mL/min; (5) injection volume: 20 µL; (6) run time: 27 minutes.

2. Results

Figure 19:
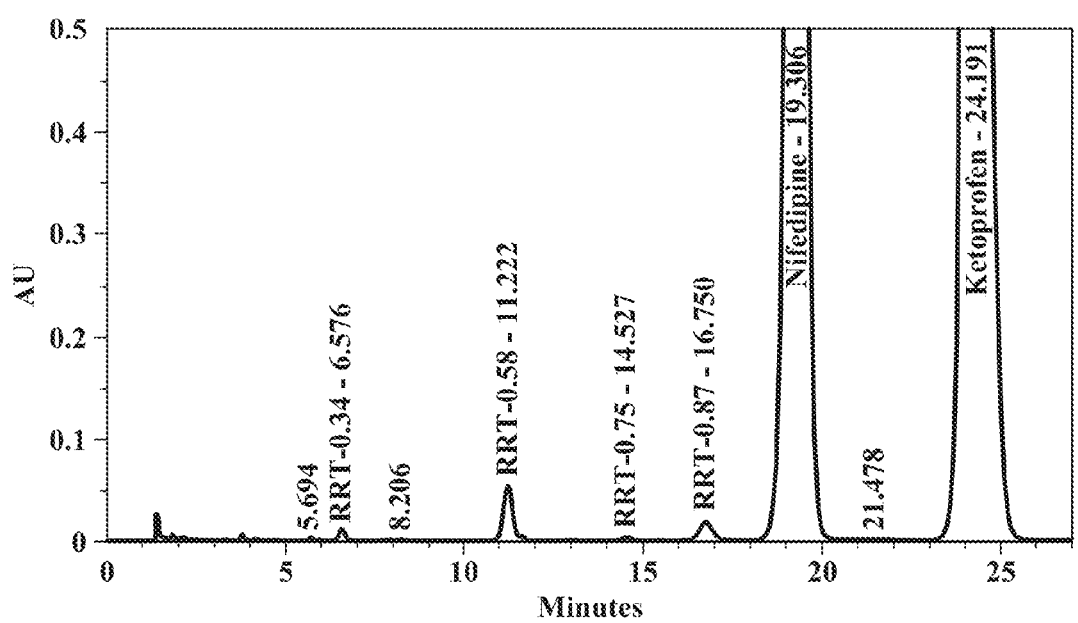
FIG. 19 shows a chromatogram of a nifedipine and ketoprofen formulation F1 in accordance with Example VIII after having been stressed at 60° C. for 1 month.

FIG. 19 shows an example chromatogram of the combination solution formulation F1 after stressing by storing at 60° C. for 1 month. The two active ingredients, ketoprofen and nifedipine, have a retention time of 24.19 minutes and 19.31 minutes respectively. There are four main related substances with relative retention times (RRT) of 0.34, 0.58, 0.75, and 0.87 relative to the nifedipine peak. This stability data is summarized in Table 10.

TABLE 10

Total related Substance (%) of Ketoprofen and Nifedipine in Tested Formulations After Storage at Different Temperatures

| Formulation ID | Days | 4° C. | 25° C. | 40° C. | 60° C. |
|---|---|---|---|---|---|
| F1 | 0 | — | 1.08 | — | — |
|  | 14 | 1.17 | | 4.17 | 8.83 |
|  | 28 | 1.49 | 3.39 | 6.69 | 16.45 |

TABLE 10-continued

Total related Substance (%) of Ketoprofen and Nifedipine in Tested Formulations After Storage at Different Temperatures

| Formulation ID | Days | 4° C. | 25° C. | 40° C. | 60° C. |
|---|---|---|---|---|---|
| F2 | 0  | —    | 1.07 | —    | —    |
|    | 14 | 1.57 | —    | 2.89 | 3.63 |
|    | 28 | 1.89 | 5.46 | 3.18 | 4.75 |
| F3 | 0  | —    | 1.34 | —    | —    |
|    | 14 | 1.76 | 2.86 | 4.54 | 8.39 |
|    | 28 | 2.11 | 3.51 | 5.44 | 12.68 |
| F4 | 0  | —    | 0.28 | —    | —    |
|    | 14 | 0.29 | 0.31 | 0.34 | 0.81 |
|    | 28 | 0.30 | 0.33 | 0.51 | 1.49 |

The stability data in Table 10 indicates that the chemical stability of ketoprofen and nefidipine, especially nifedipine, is significantly improved in the presence of a small amount of either propyl gallate (0.05% w/v) or sodium metabisulfite (0.02% w/v) at elevated temperatures such as 40° C. and 60° C., with this effect being unexpectedly pronounced for propyl gallate. When a small quantity of both propyl gallate (0.05% w/v) and sodium metabisulfite (0.02% w/v) is added to F4, the stability of the two drugs at all temperatures is significantly improved when compared with the other three combination formulations without antioxidant or with one of the two antioxidants alone, suggesting additive or synergistic degradation inhibition effect of the two antioxidants.

While the preferred embodiment of the invention has been illustrated and described, it will be appreciated that various changes to the disclosed solutions and methods can be made therein without departing from the spirit and scope of the invention. It is therefore intended that the scope of letters patent granted hereon be limited only by the definitions of the appended claims.

The embodiments of the invention in which an exclusive property or privilege is claimed are defined as follows:

1. A stable composition for use in inhibiting pain/inflammation and spasm, comprising a combination of ketoprofen, nifedipine, propyl gallate and sodium metabisulfite in a liquid carrier, wherein the ketoprofen and nifedipine are included at a ketoprofen to nifedipine molar ratio of 3:1 plus or minus 20%.

2. The composition of claim 1, wherein the liquid carrier comprises an aqueous solvent.

3. The composition of claim 2, wherein the composition further comprises polyethylene glycol 400 as a cosolvent.

4. The composition of claim 1, wherein the composition further comprises a citric acid buffer.

* * * * *

UNITED STATES PATENT AND TRADEMARK OFFICE
CERTIFICATE OF CORRECTION

PATENT NO. : 9,855,256 B2  
APPLICATION NO. : 15/145453  
DATED : January 2, 2018  
INVENTOR(S) : Gregory A. Demopulos et al.

Page 1 of 1

It is certified that error appears in the above-identified patent and that said Letters Patent is hereby corrected as shown below:

In the Claims

| Column | Line | Error |
| --- | --- | --- |
| 22 | 62 | "ranging from 0.001 to 1 μM" should read --ranging from 0.001 μM to 1 μM-- |
| 29 | 10 | "by 50 percent or more (50%)" should read --by 50 percent or more (≥50%)-- |

Signed and Sealed this  
Eleventh Day of June, 2019

Andrei Iancu  
*Director of the United States Patent and Trademark Office*